United States Patent [19]

Hope et al.

[11] Patent Number: 6,139,871
[45] Date of Patent: Oct. 31, 2000

[54] LIPOSOME COMPOSITIONS AND METHODS FOR THE TREATMENT OF ATHEROSCLEROSIS

[75] Inventors: Michael J. Hope; Wendi Rodrigueza, both of Vancouver, Canada

[73] Assignee: The University of British Columbia, Vancouver, Canada

[21] Appl. No.: 09/175,553

[22] Filed: Oct. 20, 1998

Related U.S. Application Data

[63] Continuation of application No. 08/507,170, Jul. 26, 1995, abandoned, which is a continuation of application No. 08/206,415, Mar. 4, 1996, abandoned.

[51] Int. Cl.[7] .......................... A61K 9/127; A61K 9/133
[52] U.S. Cl. ...................... 424/450; 428/402.2; 514/824
[58] Field of Search ................... 424/450, 1.21, 424/9.321, 9.51, 417, 420, 94.3; 428/402.2; 514/824; 935/54

[56] References Cited

U.S. PATENT DOCUMENTS

| | | |
|---|---|---|
| 4,186,183 | 1/1980 | Steck et al. . |
| 4,217,344 | 8/1980 | Vanlerberghe et al. . |
| 4,261,975 | 4/1981 | Fullerton et al. . |
| 4,485,054 | 11/1984 | Mezei et al. . |
| 4,774,085 | 9/1988 | Fidler . |
| 4,812,314 | 3/1989 | Barenholz .............................. 424/450 |
| 4,946,787 | 8/1990 | Eppstein et al. . |
| 5,077,056 | 12/1991 | Bally et al. . |
| 5,204,112 | 4/1993 | Hope et al. . |
| 5,231,090 | 7/1993 | Hsia ........................................ 514/78 |
| 5,252,263 | 10/1993 | Hope et al. . |
| 5,376,452 | 12/1994 | Hope et al. . |
| 5,736,157 | 4/1998 | Williams . |
| 5,746,223 | 5/1998 | Williams . |
| 5,843,474 | 12/1998 | Williams . |
| 5,858,400 | 1/1999 | Williams . |

FOREIGN PATENT DOCUMENTS

| | | |
|---|---|---|
| 0 461 559 A2 | 6/1991 | European Pat. Off. . |
| 0470437 | 2/1992 | European Pat. Off. . |
| WO 88.09345 | 12/1988 | WIPO . |
| WO 91/17424 | 11/1991 | WIPO . |

OTHER PUBLICATIONS

Williams BBA 875, p. 189, 1986.
Williams Perspectives in Biology & Media 27, p. 417, 1984.
Liu BBA 1022, p. 348, (1990).
Adams, et al., "Modification of aortic atheroma and fatty liver in cholesterol–fed rabbits by intravenous injection of saturated and polyunsaturated lecithins," *J. Pathol Bacteriol* 94:777–87 (1967).
Altman, et al., "Phospholipids in experimental atherosclerosis," *Arzneim Forsch* 24:11–16 (1974).
Aviram, et al., "Intralipid infusion abolishes ability of human serum to cholesterol–load cultured macrophages," *Atherosclerosis* 9:67–75 (1989).
Aviram, et al., "Macrophage cholesterol removal by triglyceride–phospholipid emulsions," *Biochem Biophys Res Commun* 155:709–713 (1988).
Bally, et al., "Novel procedures for generating and loading liposomal systems," in: *Liposomes as drug carriers: recent trends and progress* (Gregoriadis G., ed.), pp. 841–853, John Wiley & Sons Ltd.: Chichester, England, 1988.
Bialecki, et al., "Cholesterol enrichment increases basal and agonist–stimulated calcium influx in rat vascular smooth muscle cells," *J. Clin Invest* 88:1894–1900 (1991).
Blaton, et al., "The human plasma lipids and lipoproteins under influence of EPL–therapy," in: *Phosphatidylcholine* (Peeters, H., ed.), pp. 125–132, Springer–Verlag: Berlin, 1976.

(List continued on next page.)

*Primary Examiner*—Gollamudi S. Kishore
*Attorney, Agent, or Firm*—Arnall Golden & Gregory, LLP

[57] ABSTRACT

The present invention provides compositions and methods for treating atherosclerosis. The compositions comprise unilamellar liposomes having an average diameter of 100–150 nanometers. Methods for treating atherosclerosis employing the compositions of the present invention are also provided.

6 Claims, 12 Drawing Sheets

OTHER PUBLICATIONS

Bligh, et al., "A Rapid Method of Total Lipid Extraction and Purification," *Can. J. Biochem. Physiol.* 37:911–917 (1959).

Bloomfield, "Quasi–Elastic Light Scattering Applications in Biochemistry and Biology," *Ann. Rev. Biophys. Bioeng.* 10:421–450 (1981).

Byers, et al., "Effect of infusions of phosphatides upon the atherosclerosis aorta in situ and as an ocular aortic implant," *J. Lipid Res* 1:343–349 (1960).

Campanacci, et al., "Response to plasma lipid fractions to the administration of exogenous phospholipids", *Arxneimittelforschung* 25:1306–1308 (1975).

Chisolm, "Antioxidants and Atherosclerosis: A Current Assessment," *Clin. Cardiol.*, 14:25–30 (1991).

Ciammaichella, et al., "La fosfatidicolin polinsatura (EPL). nel trattamento delle affezioni atersclerotiche cerebrali e degli arti inferiori," Clin Ter 74:55–62 (1975).

Constantinides et al., "Production of Advanced Cholesterol Atherosclerosis in the Rabbit," *Arch. Pathol.* 70:81–02 (1961).

Deamer, et al., "Large Volume Liposomes by an Ether Vaporization Method," *Biochim. Biophys. Acta* 443:629–634 (1976).

Ellens, et al. "In vivo fate of large unilamellar sphigomyelin–cholesterol liposomes after intraperitoneal and intravenous injection into rats," *Biochem Biophys Acta* 674:10–18 (1981).

Fiske, et al., "The Colorimetric Determination of Phosphorus," *J. Biol. Chem.* 66:375–400 (1925).

Fraley et al., "Entrapment of a bacterial plasmid in phospholipid vesicles: Potential for gene transfer," *Proc. Natl. Acad. Sci. USA* 76:3348–3352 (1979).

Friedman, et al., "Resolution of aortic atherosclerosis infiltration in the rabbit by phosphatide infusion," *Proc. Soc Exp Biol Med* 95:586–588 (1957).

Gregoriadis, et al., "Liposomes In Vivo: A Relationship Between Stability and Clearance?," in: *Targeting of Drugs with Synthetic Systems* (Gregoriadis, et al., eds.), pp. 183–192, Plenum Press: New York, 1985.

Gwynne, "HDL and Atherosclerosis: An Update," *Clin. Cardiol.* 14:17–24 (1991).

Holman, et al., "Technics for Studying Atherosclerosis Lesions," *Lab., Invest.* 7:42–47 (1958).

Hope, et al., "Generation of Multilamellar and Unlilamellar Phospholipid Vesicles," *Chem. Phys. Lipids* 40:89–107 (1986).

Hope, et al., "Production of large unilamellar vesicles by a rapid extrusion procedure. Characterization of size distribution, trapped volume and ability to maintain a membrane potential," *Biochim. Biophys. Acta* 812:55–65 (1985).

Howard, et al., "Atherosclerosis induced in hypercholesterolemic baboons by immunological injury; and the effects of intravenous polyunsaturated phosphatidyl choline," *Atherosclerosis* 14;17–29 (1971).

Krack, et al., "Intraperitoneal administration of phosphatidylcholine improves ultrafiltration in continuous ambulatory peritoneal dialysis patients," *Perit Dial Int* 12:359–364 (1992).

Mauk, et al., "Stability of lipid vesicles in tissues of the mouse: a gamma–ray perturbed angular correlation study," *Proc Natl Acad Sci (USA)* 76:765–769 (1979).

Maurukas, J., et al., "Treatment of experimental atherosclerosis in the rabbit with L, D. alpha (dimyristoyl) lecithin," *J Lab Clin Med* 56:30–37 (1960).

Mayer et al., "Vesicles of variable sizes produced by a rapid extrusion procedure," *Biochim. Biophys. Acta* 858:161–168 (1986).

Mihail, et al., "The coronary syndrome in two cases of essential familial hypercholesterolemia (the therapeutic effect of polyene–phosphatidyl–choline)," *Rev Roum Med Intern* 10:255–233 (1973).

Miyazaki, A., et al., "Acetylated low density lipoprotein reduces its ligand activity for the scavenger receptor after interaction with reconsituted high density lipoprotein," *J Biol Chem* 269:5264–5269 (1994).

Nayar, et al., "Generation of large unilamellar vesicles from long–chain saturated phosphatidylcholines by extrusion technique," *Biochim. Biophys. Acta* 986:200–206 (1989).

Patelski, et al., "Modification of enzyme activities in experimental atherosclerosis in the rabbit," *Atherosclerosis* 12:41–53 (1992).

Phillips et al., "Mechanisms and consequences of cellular cholesterol exchange and transfer," *Biochim. Biophys. Acta* 906:223–276 (1987).

Plane, et al., "Oxidative modification of low–density lipoproteins and the inhibition of relaxations mediated by endothelium–derived nitric oxide in rabbit aorta," *Br J Pharmacol* 105:216–222 (1992).

Prior et al., "The Hypercholesteremic Rabbit," *Arch. Path.* 71:82–94 (1961).

Reynolds, "Rational Therapy of Familial Hypercholesterolemia," *Circulation* 79:1146–1148 (1989).

Rodrigueza, et al., "The influence of size and composition on the cholesterol mobilizing properties of liposomes in vivo," *Biochim Biophys Acta* 1153:9–19 (1993).

Rose, et al., "Improved procedure for the extraction of lipids from human erthyrocytes," *J. Lipid Res.* 6:428–431 (1965).

Rosenfeld, et al., "Lipid Composition of Aorta of Watanabe Heritable Hyperlipemic and Comparably Hypercholesterolemic Fat–fed Rabbits," *Athereosclerosis* 8:338–347 (1988).

Rudell, et al., "Determination of cholesterol using o–phthalaldehyde," *J. Lipid Res.* 14:364–366 (1973).

Sahni, et al., "Prevention of restonosis by lovastatin after successful coronary angioplasty," *Am. Heart J* 121:1600–1608 (1991).

Schenk, et al., "Studies on sucrose–palmitate–stearate–containing vesicles encapsulating the cytostatic drug methylglyoxal–bis–guanyl–hydrazone," *Pharmzie.* 45(10):747–9 (1990).

Scherphof, et al., "Disintegration of Phosphatidylcholine Liposomes in Plasma as a Result of Interaction with High–Density Lipoproteins," *Biochim. Biophys. Acta* 542:296–307 (1978).

Schmidt, et al., "High–density lipoprotein antagonizes the inhibitory effects of oxidized low–density lipoprotein and lysolecithin on soluble guanylyl cyclase," *Biochem Biophys Res Commun* 182:302–308 (1992).

Schroeder, et al., "Membrane Cholesterol Dynamics: Cholesterol Domains and Kinetic Pools," *Exp. Biol. Med.* 196:235–252 (1991).

Schumaker et al., "Sequential Flotation Ultracentrifugation," *Methods Enzymol.* 128:155–181 (1986).

Senior, et al., "Tissue districution of liposomes exhibiting long half–lives in the circulation after intravenous injection," *Biochim. Biophys. Acta* 839:1–8 (1985).

Small, "Progression and Regression of Atherosclerotic Lesions," *Arteriosclerosis* 8:103–129 (1988).

St. Clair, "Atherosclerosis Regression in Animal Models: Current Concepts of Cellular and Biochemical Mechanisms," *Prog. Cardiovasc. Dis.* 26:109–132 (1983).

Stafford, W.W. et al., "Regression of atherosclerosis affected by intravenous phospholipid," *Artery* 1:106–114 (1975).

Stuart, et al., "Effects of cholesterol on production of thromboxane b2 by platelets in vitro," *New Engl J Med* 303:6–10 (1980).

Sugiyama, et al., "Lipoproteins regulate C–type natriuretic peptide secretion from cultured vascular endothelial cells," *Arterioscler Thromb Vasc Biol* 15:1968–1974 (1995).

Tall, et al., "Lipoprotein–liposomes interactions," *Methods Enzymol* 128:647–657 (1986).

Thompson, et al., "Effects of intravenous phospholipid on low density lipoprotein turnover in man," *Eur J Clin Invest* 6:241–248 (1976).

Untract, "Intravascular metabolism of an artificial transporter of triacylglycerols. Alterations of serum lipoproteins resulting from total parenteral nutrition with Intralipid," *Biochim Biophys Acta.* 711(1):176–92 (1982).

Waligora, et al., "Effect of a hypercholesterolaemic diet and a single injection of polyunsaturated phosphatidyl choline solution on the activities of lipolytic enzymes, acyl–CoA synthetase and acyl–CoA cholesterol acyl–transferase in rabbit tissues," *Biochem Pharmacol* 24:2263–2267 (1975).

Williams et al., "Intravenously Administered Lecithin Liposomes: A Synthetic Antiatherogenic Lipid Particle," *Perspect. Bio. Med.* 27:417–431 (1984).

Williams et al., "Low density lipoprotein receptor–independent hepatic uptake of a synthetic, cholesterol–scavenging lipoprotein: Implications for the treatment of receptor–deficient atherosclerosis," *Proc. Natl. Acad. Sci.* 85:242–246 (1988).

Williams, et al., "Interactions of liposomes with lipoproteins: relevance to drug delivery systems and to the treatment of atherosclerosis," in: *Liposomes as drug carriers: recent trends and progress* (Gregoriardis G., ed.), pp. 93–111, John Wiley & Sons Ltd: Chichester, England, 1988.

Williams, et al., Phospholipid liposomes acquire.

William, et al., "Phospholipid liposomes acquire apolipoprotein E in atherogenic plasma and block cholesterol loading of cultured macrophages," *J Clin Invest* 79:1466–1472 (1987).

Williams, et al., "Recognition of vesicular lipoproteins by the apolipoprotein B,E receptor of cultured fibroblasts," *J. Lipid Res* 27:892 (1986).

Williams, et al., "The unstirred water layer as a site of control of apolipoprotein B secretion," *J Biol Chem* 265:16741–16744 (1990).

Mendez, et al., "Interaction of Rabbit Lipoproteins and Red Blood Cells with Liposomes of Egg Yolk Phospholipids," *Lipids* 23:961–967 (1988).

LIPOSOME COMPOSITIONS AND METHODS FOR THE TREATMENT OF ATHEROSCLEROSIS

This application is a continuation of Ser. No. 08/507,170 filed Jul. 26, 1995 now abandoned, which is a continuation of Ser. No. 08/206,415 filed Mar. 4, 1996 which is abandoned.

BACKGROUND OF THE INVENTION

The present invention provides pharmaceutical compositions and methods useful for the treatment of atherosclerosis. More particularly, the compositions generally comprise liposomes having an average diameter of about 100–150 nanometers and a pharmaceutically acceptable carrier. The methods generally comprise administering such compositions.

Atherosclerosis is the leading cause of death in the United States. Atherosclerosis is the formation of plaques in arterial walls that can occlude the vessel lumen and obstruct blood flow through the vessel. Morbidity and mortality generally occur through end organ damage and organ dysfunction resulting from ischemia. The most common forms of ischemic end organ damage are myocardial infarction and cerebrovascular accidents. Disability or death often result from these vascular events. Even atherosclerosis-related ischemia that does not permanently injure myocardium is responsible for significant morbidity in the form of angina pectoris and congestive heart failure. Other organs, such as the kidneys, the intestines, and the spinal cord, may also be injured by atherosclerotic occlusions. Further, in diseases such as aortic aneurysms, atherosclerotic arteries may cause clinical symptoms independent of end organ dysfunction.

Arteriosclerotic lesions are plaques that form by accumulation of cholesterol, cholesterol esters, and phospholipids and proliferation of smooth muscle cells in the intima of major arteries. Lipid contributes a major portion of the plaque volume (generally 30–65% dry weight). Small, *Arteriosclerosis*, 8:103–129 (1988). In fact, the risk of developing arteriosclerosis is directly related to the concentration of certain forms of plasma cholesterol.

Lipids, including cholesterol, are generally insoluble in aqueous plasma. Plasma lipids are carried by soluble lipoprotein complexes. These lipoprotein complexes consist of an inner core of non-polar lipids (cholesteryl esters and triglycerides) and an surface layer of hydrophilic proteins and polar lipids (phospholipids and non-esterified cholesterol). Different proteins are present in the surface coat of different lipoprotein complexes (lipoproteins). The different lipoproteins perform different functions in lipid metabolism.

Five classes of lipoproteins are known. Some lipoproteins carry triglycerides and cholesterol from the liver to peripheral tissues while others transport lipids to the liver. Cholesterol may be metabolized in the liver to bile salts that are excreted, thus lowering total body cholesterol. Two lipoproteins, low density lipoproteins (LDL) and high density lipoproteins (HDL), have a high degree of association with the development of atherosclerosis. LDL has a high cholesterol concentration, delivers lipids to cells of peripheral tissues, and is associated with a high risk of atherosclerosis. HDL also has a relatively high cholesterol concentration, but carries lipids to the liver for metabolism into bile salts and is associated with decreasing the risk of developing atherosclerosis.

Cholesterol metabolism and homeostasis is the result of a complex equilibrium between free sterol in the cell and in plasma. Phillips et al., *Biochim. Biophys. Acta*, 906:223–276 (1987). Delivery of cholesterol to cells occurs via the receptor-mediated LDL pathway and by passive exchange of sterol between plasma membranes and lipoproteins. Only tissues that produce steroid hormones and bile acids can metabolize cholesterol. In order to prevent accumulation of excess free sterol in remaining peripheral tissues there is a reverse transport of cholesterol from plasma membranes into HDL and lipoprotein-like particles. HDL transports excess cholesterol to the liver where it can either be processed into bile salts for excretion or incorporated into very low density lipoproteins (VLDL) to re-enter the lipoprotein pool.

The passive exchange of cholesterol between cells and lipoproteins occurs via the diffusion of sterol molecules across the aqueous space. Phillips et al., supra, and Schroeder et al., *Exp. Biol. Med.*, 196:235–252 (1991). Net cellular efflux occurs if the chemical potential of free cholesterol is lower in the plasma than in the cells so that sterol leaves the membrane following its activity gradient. Under these conditions, it has been shown that cholesterol-ester-loaded cells, which are morphologically characteristic of early atherosclerotic lesions, not only lose cholesterol, but promote ester hydrolysis, resulting in the reduction of intracellular deposits of this lipid. Small, *Arteriosclerosis*, 8:103–129 (1988). Moreover as mentioned above, there is epidemiological evidence that conditions which might be expected to enhance reverse cholesterol transport (low plasma cholesterol concentrations, or increased HDL concentrations) are correlated with reduced risk of premature atherosclerosis and may give rise to plaque regression.

Characteristically, plaques are associated with ulceration of the vessel intima. The lipid-containing plaques grow in the ulcerations projecting friable masses into the arterial lumen. The plaques may also injure and weaken the smooth muscle media of the vessel. As plaque formation progresses, more central regions of the plaques are shielded from the circulation. Extensive plaque formation also cause concentric constriction of the vessel at the plaque site.

Presently, the most effective treatment of atherosclerosis is prevention. There is evidence that the progression and accumulation of lipids in lesions can be halted when plasma LDL concentrations are kept to near normal levels. Reynolds, *Circulation*, 79:1146–1148 (1989). Current preventive management of atherosclerotic disease has focused on the use of drugs in conjunction with dietary restrictions to regulate plasma cholesterol levels. Moreover, antioxidant therapies which suppress the formation and uptake of modified LDL particles by the cells of the arterial wall are also proving beneficial. Chisolm, *Clin. Cardiol.*, 14:25–30 (1991). However, while hypocholesterolemic drugs induce favorable plasma cholesterol changes which appear to slow the progression of atherosclerosis, they do not generally induce conditions that promote the efflux and removal of atheroma cholesterol. Clearly, in order to achieve significant regression of atheroma and lessen lumen obstruction, these space occupying lipids must be mobilized. Present evidence suggests that processes which stimulate the efflux of extrahepatic cell cholesterol and transport it to the liver for excretion, reverse cholesterol transport (RCT), are important events in the prevention of atherosclerosis. Gwynne, *Clin. Cardiol.*, 14:17–24 (1991).

Current therapeutic modalities of arteriosclerosis are generally divided into surgical and medical management. Surgical therapy may entail vascular graft procedures to bypass regions of occlusion (e.g., coronary artery bypass grafting), removal of occluding plaques from the arterial wall (e.g., carotid endarterectomy), or percutaneously cracking the plaques (e.g., balloon angioplasty). Surgical therapies carry significant risk and only treat isolated lesions. Atherosclerotic plaques downstream from the treated lesion may continue to obstruct blood flow. Surgical therapies also do not limit the progression of atherosclerosis and are associated with the late complication of restenosis.

Medical therapy is directed to reducing other risk factors related to vascular disease (e.g., smoking, diabetes, and hypertension) and lowering forms of serum cholesterol that are associated with the development of atherosclerosis as described above. While medical therapies may slow the progression of plaque formation, plaque regression is relatively rare. Therefore, symptomatic atherosclerosis often requires both surgical and medical treatment.

Paradoxically, intravenous infusion of phospholipids and liposomes has been shown to produce regression of atherosclerotic plaques although serum lipid levels are transiently elevated. Williams et al., *Perspect. Biol. Med.*, 27:417–431 (1984). In some instances, however, cholesterol associated with development and progression of atherosclerosis may increase following liposome administration.

Previous studies investigating phospholipid-induced mobilization of cholesterol in vivo have employed multilamellar or sonicated liposome vesicles. Liposome size is a key characteristic in clearance kinetics and is one of several reasons why sonicated vesicles have been expected to represent the bilayer structure best suited to enhance reverse cholesterol transport. Sonication reduces multilamellar vesicles (MLV) to 'limit size' vesicles. These systems exhibit the minimum radius of curvature that can be adopted by the bilayer configuration without disruption. For example, the minimum size egg phosphatidylcholine liposome that can be generated is typically about 30-nm diameter, often classified as a small unilamellar vesicle (SUV). For a given liposome composition, it is generally assumed that the smaller the particle diameter the greater the circulation half-life (Gregoriadis and Senior, *Life Sci.*, 113:183–192 (1986)). Consequently, it was expected that SUV composed of phosphatidylcholine would circulate longer than larger liposomes, and therefore mobilize more cholesterol. Furthermore, packing constraints experienced by phospholipids in SUV, (due to the acute radius of curvature) gives rise to an instability that can result in fusion, Hope et al., *Chem. Phys. Lipids*, 40:89–107 (1986), as well as an increased tendency to assimilate with lipoproteins. See, e.g., Scherphof et al., *Biochim. Biophys. Acta*, 542:296–307 (1978) and Krupp et al., *Biochim. Biophys. Acta*, 72:1251–1258 (1976). Therefore, it was expected that SUV would produce a greater number of HDL-like particles, thus promoting efflux of sterol from peripheral tissues. Supporting this expectation, liposomes having diameters of 50–80 nm have been reported to optimize sterol mobilization and plaque regression. European Patent Publication No. 0461559A2.

What is needed in the art is a medical treatment for atherosclerosis that not only will slow progression of lesions, but also predictably cause regression and shrinkage of established plaques. Such a treatment should provide the optimal rate of cholesterol removal (and, hence shrinkage) from plaques. Quite surprisingly, the present invention fulfills these and other related needs.

SUMMARY OF THE INVENTION

The present invention provides pharmaceutical compositions consisting essentially of unilamellar liposomes having an average diameter of about 100–150 nanometers, which liposomes are not bound to a drug; and a pharmaceutically acceptable carrier. These liposomes optimize cholesterol efflux from atherosclerotic plaques. The liposomes may be bound to an apoprotein, typically apoprotein A1 or A2. The liposomes often contain at least one phospholipid, such as phosphatidylcholine or phosphatidylglycerol. Liposomes having diameters of about 125 nm are preferred.

Also provided are methods for treating atherosclerosis employing the pharmaceutical compositions of the present invention. The compositions are administered to animals having atherosclerosis. Often, the compositions will be serially administered over a period of time. Generally, the compositions will be administered parenterally, usually intravenously. The methods may be employed therapeutically or prophylactically. The methods of the present invention are also useful for treatment of hypoalphalipoproteinemia and hyperlipidemias.

DESCRIPTION OF THE PREFERRED EMBODIMENT

Figure 1A:
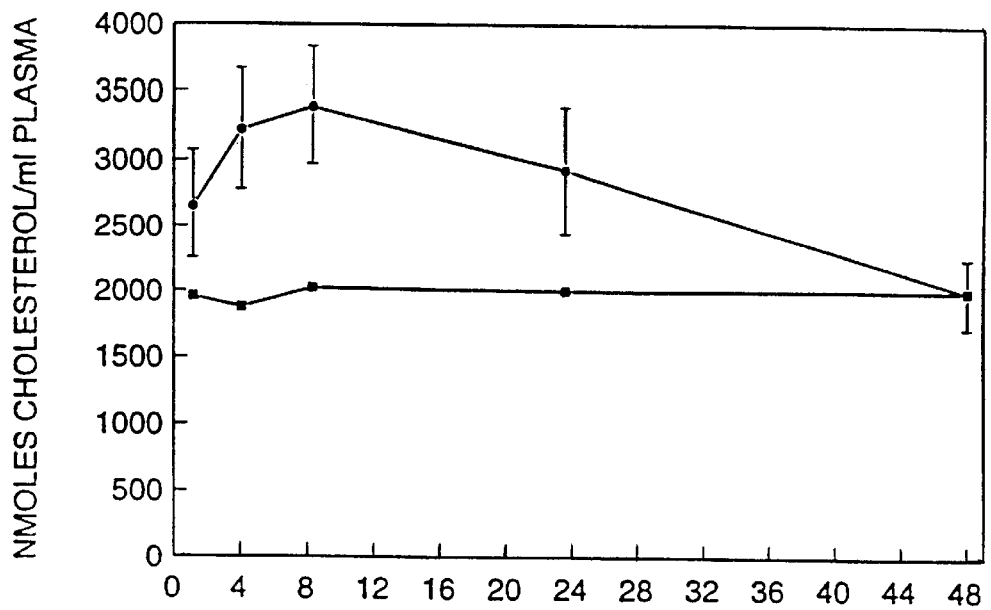
FIGS. 1A and 1B demonstrate cholesterol mobilization by a homogeneous population of large unilamellar vesicles with a mean diameter of 125 nm.

The present invention provides pharmaceutical compositions consisting essentially of unilamellar liposomes having an average diameter of about 100–150 nanometers, which liposomes are not bound to a drug; and a pharmaceutically acceptable carrier. Also provided are methods for treating atherosclerosis using the compositions of the present invention.

As used herein, "drug" is meant to indicate a synthetic compound suitable for therapeutic use without associated bound carriers, adjuvants, activators, or co-factors. "Drug" does not include apoproteins, lecithin-cholesterol acyltransferase, or albumin.

"Liposome", "vesicle" and "liposome vesicle" will be understood to indicate structures having lipid-containing membranes enclosing an aqueous interior. The structures may have or one more lipid membranes unless otherwise indicated, although generally the liposomes will have only one membrane. Such single layered liposomes are referred to herein as "unilamellar".

Arterial atherosclerotic lesions have been shown to regress when treated with liposome infusions. In some instances, however, LDL cholesterol has been observed to increase following liposome administration. Prior to the present invention, the cause of this paradox has not been understood.

The present invention is based, in part, on the discovery that liposome size plays a critical role in the metabolism of cholesterol removed from atherosclerotic plaques by the liposomes. Contrary to previous descriptions of liposome therapy, liposomes having a diameter of greater than 100 nanometers are more effective for removing cholesterol from atherosclerotic plaques than smaller liposomes.

The superior action of liposomes greater than 100 nanometers in diameter may be explained by the micro-anatomy of the liver. When circulating in the liver, large liposomes (as used herein, liposomes greater than 100 nm in diameter) may be cleared by the Kupffer cells that line the sinusoidal openings. The Kupffer cells transfer cholesterol to hepatocytes for excretion in the bile or re-utilization. Small liposomes (as used herein, liposomes smaller than 100 nm) may directly access hepatocytes without prior processing by the Kupffer cells. Because these small liposomes are infused in relatively large doses, hepatocytes may be acutely exposed to a relatively high concentration of small liposomes and their accumulated cholesterol.

The pharmaceutical compositions of the present invention generally consist essentially of unilamellar liposomes having an average diameter of about 100–150 nanometers, which liposomes are not bound to a drug; and a pharmaceutically acceptable carrier. In some instances multilamellar liposomes may also be employed in the compositions of the present invention, either exclusively or in addition to unilamellar liposomes. The liposomes will have an average diameter of about 100–150 nanometers, typically about 125–140 nanometers. In some embodiments, liposomes having an average diameter larger than 150 nanometers, either uni- or multilamellar, may also be present in the compositions of the present invention.

Persons of skill will appreciate that the liposomes in the compositions of the present invention may be synthesized by a variety of methods, such as described in, e.g., U.S. Pat. No. 4,186,183; U.S. Pat. No. 4,217,344; U.S. Pat. No. 4,261,975; U.S. Pat. No. 4,485,054; U.S. Pat. No. 4,774,085; U.S. Pat. No. 4,946,787; PCT Publication No. WO 91/17424, Deamer and Bangham, *Biochim. Biophys. Acta*, 443:629–634 (1976); Fraley et al., *Proc. Natl. Acad. Sci. USA*, 76:3348–3352 (1979); Hope et al., *Biochim. Biophys. Acta*, 812:55–65 (1985); Mayer et al., *Biochim. Biophys. Acta*, 858:161–168 (1986); and Williams et al., *Proc. Natl. Acad. Sci.*, 85:242–246 (1988), each of which is incorporated herein by reference. Suitable methods include, e.g., sonication, extrusion, high pressure/homogenization, microfluidization, detergent dialysis, calcium-induced fusion of small liposome vesicles, and ether-infusion methods, all well known in the art.

Generally, the liposomes are most conveniently generated by sonication and extrusion procedures. Briefly, a chloroform solution of lipid is vortexed and the solvent removed under a steady stream of $N_2$. The sample is dried under a high vacuum. The resulting dry lipid film is rehydrated in 150 mM NaCl and 20 mM [4-(2-hydroxyethyl)]-piperazineethanesulfonic acid (Hepes, pH 7.4). This generally produces multilamellar liposomal vesicles. Unilamellar vesicles are prepared by sonication or extrusion.

Sonication is generally performed with a tip sonifier, such as a Branson tip sonifier, in an ice bath. Typically, the suspension is subjected to several sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

The size of the liposomal vesicles may be determined by quasi-electric light scattering (QELS) as described in Bloomfield, *Ann. Rev. Biophys. Bioeng.*, 10:421–450 (1981), incorporated herein by reference. Average liposome diameter may be reduced by sonication of formed liposomes. Intermittent sonication cycles may be alternated with QELS assessment to guide efficient liposome synthesis.

The liposomes may be composed of a variety of lipids. Generally, the liposomes will be composed of at least one phospholipid, typically egg phosphatidylcholine, egg phosphatidylglycerol, distearoylphosphatidylcholine, or distearoylphosphatidylglycerol. Many embodiments of the present invention will include more than one phospholipid.

Other phospholipids suitable for formation of liposomes comprising the compositions of the present invention include, e.g., phosphatidylcholine, phosphatidylglycerol, lecithin, $\beta,\gamma$-dipalmitoyl-$\alpha$-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like. Additional lipids suitable for use in the liposomes of the present invention are well known to persons of skill in the art and are cited in a variety of well known sources, e.g., *McCutcheon's Detergents and Emulsifiers* and *McCutcheon's Functional Materials*, Allured Publishing Co., Ridgewood, N.J., both of which are incorporated herein by reference.

Generally, it is desirable that the liposomes be composed of lipids that are liquid-crystalline at 37° C., often at 35° C., and even 32° C. Liposomes in the liquid-crystalline state typically accept cholesterol more efficiently than liposomes in the gel state. As patients typically have a core temperature of about 37° C., liposomes composed of lipids that are liquid-crystalline at 37° C. are generally in a liquid-crystalline state during treatment and, therefore, optimize removal of cholesterol from plaques.

The pharmaceutical compositions of the present invention also comprise a pharmaceutically acceptable carrier. Many pharmaceutically acceptable carriers may be employed in the compositions of the present invention. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of liposomes in the carrier may vary. Generally, the concentration will be about 20–200 mg/ml, usually about 50–150 mg/ml, and most usually about 100 mg/ml. Persons of skill may vary these concentrations to optimize treatment with different liposomal components or of particular patients. For example, the concentration may be increased to lower the fluid load associated with treatment. This may be particularly desirable in patients having atherosclerosis-associated congestive heart failure or severe hypertension. Alternatively, liposomes composed of irritating lipids may be diluted to low concentrations to lessen inflammation at the site of administration.

The liposomes may also be bound to a variety of proteins and polypeptides to increase the rate of cholesterol transfer or the cholesterol-carrying capacity of the liposomes. Binding of apoproteins to the liposomes is particularly useful. As used herein, "bound to liposomes" or "binding to liposomes" indicates that the subject compound is covalently or non-covalently bound to the surface of the liposome or contained, wholly or partially, in the interior of the liposome. Apoprotein $A_1$, apoprotein $A_2$, and apoprotein E will generally be the most useful apoproteins to bind to the liposomes. These apoproteins promote transfer of cholesterol and cholesteryl esters to the liver for metabolism. Lecithin-cholesterol acyltransferase is also useful for metabolizing free cholesterol to cholesteryl esters. Liposomes in the pharmaceutical compositions of the present invention may be bound to molecules of apoprotein $A_1$, apoprotein $A_2$, and lecithin-cholesterol acyltransferase, singly or in any combination and molar ratio. Additional proteins or other non-protein molecules may also be useful to bind to the liposomes to enhance liposome stability or half-life and the like. These include, e.g., cholesterol, polyethyleneglycol, alkylsulfates, ammonium bromide, albumin, and the like.

Also provided are methods for treating atherosclerosis in an animal. The methods generally comprise administering a liposome composition to the animal, which liposome composition consists essentially of unilamellar liposomes having an average diameter of about 100–150 nanometers. By "treating atherosclerosis", it is meant performing a therapeutic intervention that results in reducing the cholesterol content of at least one atherosclerotic plaque or prophylactically inhibiting or preventing the formation or expansion of an atherosclerotic plaque. Generally, the volume of the atherosclerotic plaque, and hence the degree of obstruction of the vascular lumen, will also be reduced. The present methods are particularly useful for treating atherosclerotic lesions associated with familial hyperlipidemias.

The methods of the present invention may reduce the cholesterol content of atherosclerotic plaques and/or the volume of atherosclerotic plaques. The cholesterol content will generally be reduced by at least 10%–30%, often by 30%–50%, and in some instances as much as 75%–85% or more. The volume of the atherosclerotic plaques will also generally be reduced. The reduction in plaque volume will generally be at least 5%–30%, often as much as 50%, and in some instances 75% or more.

Cholesterol may be mobilized from the plaques by either direct efflux into the liposomes or into lipoproteins that subsequently transfer the cholesterol to the liposomes. As cholesterol is transferred to the liposomes from the lipoproteins, the lipoproteins may receive more cholesterol from plaques. Generally, when cholesterol is received from lipoproteins, the cholesterol is transferred from HDL.

The methods may be useful to treat atherosclerosis in a variety of animals and in a variety of blood vessels. Typically, the animal will be human, although non-human primates, dogs, cats, rodents, horses, cows, and the like may be treated by the methods of the present invention. Atherosclerosis of any blood vessel, such as the aorta, carotid arteries (common, internal, and external), coronary arteries, mesenteric arteries, renal arteries, iliac arteries, popliteal arteries, and the like, may also be treated by the methods of the present invention.

The methods may also be useful for prophylactic treatments. Such prophylactic treatments are particularly useful following invasive vascular procedures. Vascular regions having injured endothelium are at increased risk for developing atherosclerotic plaques. Therefore, invasive vascular procedures, such as coronary angioplasty, vascular bypass grafting, and other procedures that injure the vascular endothelial layer, may be practiced in conjunction with the methods of the present invention. As the invasive procedure injures the endothelium, the liposomes act to remove cholesterol from the injured region and inhibit or prevent plaque formation of expansion during endothelial healing.

Hyperlipidemias may also be treated by the methods of the present invention. Administration of liposomes, alone or bound to apoprotein $A_1$ and apoprotein $A_2$, to individuals having hypoalphalipoproteinemia from genetic or secondary causes, familial combined hyperlipidemia, and familial hypercholesterolemia is a useful treatment.

The liposomes administered in the methods of the present invention will be composed of lipids as described above. The lipids will generally be in the liquid-crystalline state at 37° C. The lipids will also generally include one or more phospholipids, often phosphatidylcholine or phosphatidylglycerol, although liposomes may be composed of many other lipids, examples of which are described above.

The liposomes may be administered in many ways. These include parenteral routes of administration, such as intravenous, intramuscular, subcutaneous, and intraarterial. Generally, the liposomes will be administered intravenously. Often, the liposomes will be administered into a large central vein, such as the superior vena cava or inferior vena cava, to allow highly concentrated solutions to be administered into large volume and flow vessels. The liposomes may be administered intraarterially following vascular procedures to deliver a high concentration directly to an affected vessel. The liposomes may also be administered directly to vessels in a topical manner by surgeons during open procedures. In some instances, the liposomes may be administered orally or transdermally. The liposomes may also be incorporated in vascular stents for long duration release following placement. This is particularly effective for angioplasty treatment of restenosis of lesions in the coronary arteries.

As described above, the liposomes will generally be administered intravenously in the methods of the present invention. Often multiple treatments will be given to the patient, generally weekly. Typically, the therapy will continue for about 4–16 weeks (4–16 treatments), usually about 10 weeks (10 treatments). The duration and schedule of treatments may be varied by methods well known to those of skill.

The dose of liposomes may vary depending on the clinical condition and size of the animal or patient receiving treatment. Humans will generally be treated with about 0.1–1.5 gm of liposomes/kg body weight, usually about 0.2–0.75 gm gm/kg, and most usually about 0.28–0.42 gm/kg. Thus, an average 70 kg person would be treated with about 20–30 gms. of liposomes per treatment. The dose will typically be constant over the course of treatment, although the dose may vary. Serum measurements of total free cholesterol, total esterified cholesterol, HDL cholesterol, LDL cholesterol, and VLDL cholesterol may be used to assess and modify dosage amounts and schedules during the treatment regimen. As cholesterol is mobilized from plaques, total serum cholesterol rises. It is desirable that total serum cholesterol and HDL cholesterol rise during therapy, and esterified cholesterol drop during therapy. The liposome dose for different animals will generally approximate the human weight-determined dosage.

The following examples are offered by way of illustration and not limitation.

EXAMPLES

Example 1

Influence of Liposome Size and Composition on In Vivo Cholesterol Mobilization

This example demonstrates the relative cholesterol mobilizing efficacy of liposomes of different sizes and compositions in mice. Liposomes having a mean diameter of about 125 nm were found to be the most effective in mobilizing cholesterol in vivo. Liquid-crystalline liposomes were more effective in mobilizing cholesterol than gel-state liposomes.

Cholesterol and [4-(2-hydroxyethyl)]-piperazineethanesulfonic acid (Hepes) were obtained from Sigma. [$^{14}$C]cholesterol hexadecyl ether and [$^3$H]cholesterol were purchased from New England Nuclear. Egg phosphatidylcholine (EPC), distearoylphosphatidylcholine (DSPC), distearoylphosphatidylglycerol (DSPG) and egg phosphatidylglycerol (EPG) were supplied by Avanti Polar Lipids. Bio-Gel A-15m medium was purchased from Bio-Rad. All chemicals, thin layer chromatography plates and solvents were of analytical grade and purchased from BDH Chemicals.

All liposome preparations were labelled using trace amounts of [$^{14}$C]cholesterol hexadecyl ether (CHE). This labelling is useful as (1) it does not undergo passive exchange between membranes; (2) mice do not exhibit cholesterol-ester exchange protein activity; and (3) the ether-linked fatty acid is not cleaved in the plasma. Consequently, in this model system CHE is an excellent liposome marker and vesicle concentrations in the plasma were estimated from the specific activity of this label.

A chloroform solution of EPC and [$^{14}$C]CHE was vortexed and solvent was removed under a stream of $N_2$. The sample was dried under high vacuum for 2 h. The dry lipid film was hydrated in 150 mM NaCl, 20 mM Hepes (pH 7.4) to generate multilamellar vesicles (MLV). Vesicles were prepared from MLV either by sonication, to generate small unilamellar vesicles (SUV) or extrusion to produce large unilamellar vesicles (LUV). Sonication was performed using a Branson tip sonifier, following standard protocols. The MLV suspension was diluted to 30 mg/ml, immersed in an ice bath and subjected to 3 cycles of sonication, each of 10-min duration. The initial milky suspension became clear and the vesicle size was 30 nm, as determined by quasi-elastic light scattering (QELS). The SUV were centrifuged at 10000×g for 30 min to remove titanium fragments originating from the sonicator tip.

Extrusion was carried out using a 10 ml Lipex Biomembranes Extruder equipped with a water jacketed thermobarrel as described by Hope et al., $Biochim.$ $Biophys.$ $Acta$, 812:55–65 (1985), incorporated herein by reference. MLV were sized through two stacked polycarbonate filters of defined pore size to generate a variety of LUV and homogeneous MLV as described in Hope et al., supra, and Mayer et al., $Biochim.$ $Biophys.$ $Acta$, 858:161–168 (1986), incorporated herein by reference.

The size of vesicles generated by sonication and extrusion procedures was determined by QELS analysis utilizing a Nicomp Model 370 submicron laser particle sizer equipped with a 5-mW He-Ne Laser. The Nicomp QELS analyzes fluctuations in light-scattering intensities due to vesicle diffusion in solution. The measured diffusion coefficient is used to obtain the average hydrodynamic radius and thus, the mean diameter of vesicles. The following diameters are expressed as the mean ±S.D. of vesicle preparations prior to injection. Vesicles prepared by sonication were 30±7 nm in diameter ($SUV_{30}$). Vesicles prepared by extrusion through filters with a pore size of 0.05 μm were 70±19 nm, 0.1 μm pore size were 125±30, and 0.4 μm pore size were 237±90 nm. Generally, the vesicles prepared by extrusion are referred to herein by the filter pore size used in their preparation, i.e., $LUV_{50}$, $LUV_{100}$ and $MLV_{400}$.

Female BDF-1 or CD-1 mice, weighing 20–22 g (Sprague-Dawley), were used throughout this study. Liposomes were injected via the tail vein at a dose of 300 mg/kg, which was typically 6 mg of liposomes in 200 ml of buffer injected for each animal. Control mice were injected with an equal volume of buffer and both groups were sacrificed at specified times with blood collection in EDTA microtainer tubes by heart puncture. Plasma was obtained following centrifugation at 2000×g for 10 min, and an aliquot removed for scintillation analysis using a Beckman LS 3801 liquid scintillation counter. The average of data from 16 mice (from four separate experiments) is indicated at each time point, unless indicated otherwise.

A 27×1.5 cm Bio-Gel A-15m gel filtration column, equilibrated with 150 mM NaCl, 10 mM Tris, 0.1% EDTA, 0.3% $NaN_3$ (pH 7.4) was used to fractionate plasma samples. Columns were eluted at a flow rate of 1 ml/min and 1-ml fractions were collected for radioactivity and lipid analyses. Data on the cholesterol:phospholipid (C/P) ratio of vesicles and lipoproteins after infusion was obtained from pooled fractions corresponding to the liposomal and lipoprotein peaks. The Bio-Gel columns were calibrated with respect to lipoprotein elution by preparing purified human lipoprotein fractions using standard ultracentrifugation procedures as described in Schumaker et al., $Methods$ $Enzymol.$, 128:155–181 (1986), incorporated herein by reference. The lipoprotein fractions were each labelled with [$^3$H] cholesterol. The elution profiles of the columns were monitored for radioactivity.

Pooled column fractions and plasma samples were extracted employing the Bligh and Dyer procedure. Bligh and Dyer, *Can. J. Biochem. Physiol.*, 37:911–917 (1959), incorporated herein by reference. The lipid extracts were analyzed for total cholesterol using the assay method of Rudell and Morris, *J. Lipid Res.*, 14:364–366 (1973). Free and esterified cholesterol concentrations were determined following separation by TLC using hexane/ether/acetic acid (70:30:1 (v/v)). Standards were used to identify the area of the plate corresponding to these two lipids, the silica was aspirated and the lipid eluted for assay using chloroform/methanol (2:1 (v/v)). Plasma vesicle phospholipid content was determined by dividing [$^{14}$C]CHE radioactivity by liposome-specific activity and phospholipid concentrations were determined by the method of Fiske and SubbaRow, *J. Biol. Chem.*, 66:375–400 (1925). Erythrocytes were extracted using the method of Rose and Oklander (*J. Lipid Res.*, 6:428–431 (1965)), followed by a Bligh and Dyer wash to remove residual salts. An aliquot of red blood cells was retained for cell number determination using a Coulter cell counter in order to express cholesterol and phospholipid concentrations as mmol/$10^9$ cells.

Blood was pooled from a group of mice and red cells packed by low-speed centrifugation. The serum was labelled with [$^3$H]cholesterol by incubation for 10 min at 37° C. with 100 $\mu$Ci of radioisotope dried from ethanol. The labelled serum was added to the packed cells and the mixture incubated at room temperature for 30 min. The cells were washed and approximately $10^6$ dpm of [$^3$H]cholesterol-labelled cells injected into the experimental groups via the tail vein. Approximately 1 min after the injection of cells, saline or liposomes were administered.

Donor and acceptor liposomes were separated employing ion exchange chromatography. A 10-fold excess of donor vesicles (100 nm diameter) composed of EPC/EPG/Chol (40:15:45 molar ratio) were incubated with 100-nm or 400-mm EPC acceptors. Donor liposomes were labelled with [$^3$H]cholesterol at 5 $\mu$Ci/100 mg total lipid and acceptors were labelled with [$^{14}$C]CHE at 0.5 $\mu$Ci/100 mg lipid. At specified time intervals, 50 $\mu$l aliquots of the incubation mixture (1 mg acceptor+10 mg donor/ml) were removed and passed down a DEAE-Sepharose 6B-CL column prepared in a 1-ml tuberculin syringe equilibrated with 30 mM NaCl, 20 mM Hepes (pH 8.0). Columns were spun at 1000×g for 1 min prior to applying aliquots of the incubation mixture. The liposome mixture was spun through the column and the eluant (acceptors) obtained with two subsequent wash/spin cycles with 500-ml aliquots of buffer. Recovery of $^{14}$C-labelled vesicles (acceptors) was typically >90%. Control experiments in which donors were labelled with a non-exchangeable marker indicated that all of the donor vesicles bound to the ion exchange column under the conditions of the experiment. Cholesterol accumulation by acceptors was determined using an LS 3801 Beckman scintillation counter equipped with a $^{14}$C/$^3$H dual-label program.

Two groups of mice (n=4) were maintained in metabolic cages and faeces collected daily. After 3 days one group was injected with 200 $\mu$l of saline and the second group with approx. 6 mg of EPC LUV$_{100}$ (dose 300 mg/kg). Faecal material was collected for a further 7 days. Samples were extracted using an isopropanol/chloroform extraction procedure and subsequently assayed for total cholesterol, free cholesterol and cholesteryl esters, as described above.

Experiments were carried out on mice maintained on regular, laboratory food for rodents (cholesterol excretion rate 10–12 $\mu$mol/g faeces) and on Teklad low cholesterol (casein-based diet which resulted in an excretion rate of approx. 0.8 $\mu$mol cholesterol/g faeces).

Figure 1B:
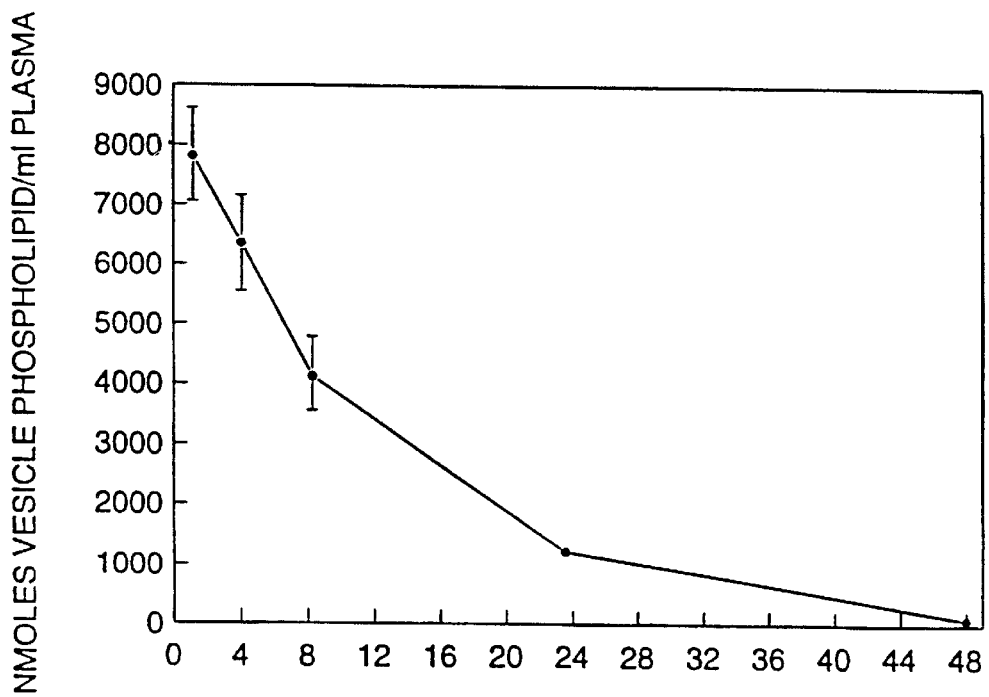

FIG. 1A demonstrates cholesterol mobilization by a homogeneous population of LUV with a mean diameter of 125 nm as determined by QELS (referred to as LUV$_{100}$ and prepared by extrusion as described above). A dramatic increase in plasma cholesterol was observed for animals receiving liposomes (FIG. 1A). Sterol levels peaked 4–8 h after injection at a concentration nearly double that measured in the control mice injected with an equivalent volume of saline. Plasma cholesterol concentrations gradually returned to normal levels after 48 h correlating well with the liposome clearance profile shown in FIG. 1B. Liposomes were labelled with trace amounts of [$^{14}$C]CHE, a non-exchangeable, non-metabolizable marker frequently used to monitor liposome clearance and distribution in vivo.

Figure 2A:
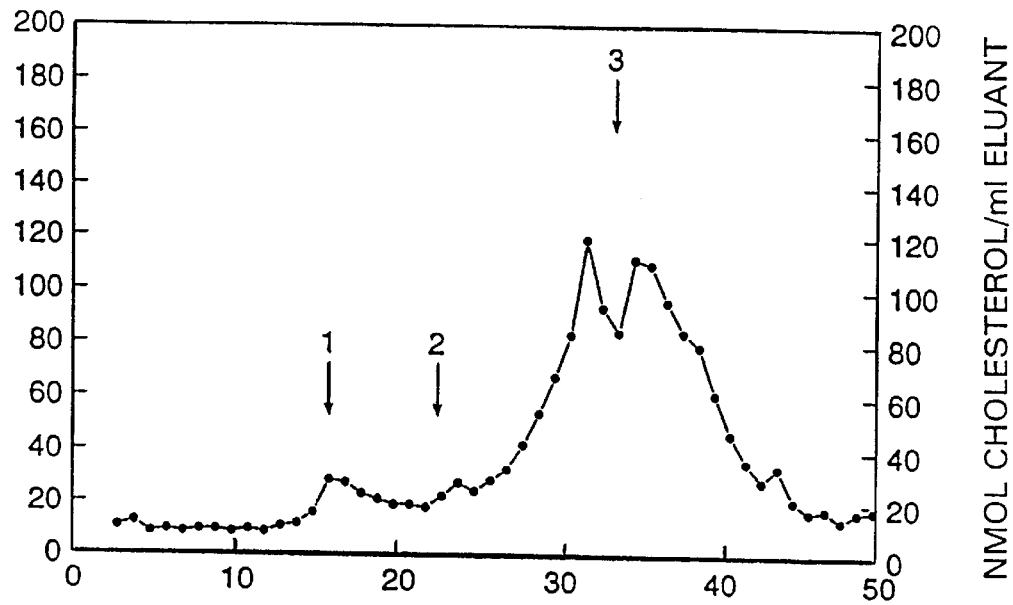
FIGS. 2A and 2B demonstrate plasma cholesterol distribution in normal and liposome-treated animals.
Figure 2B:
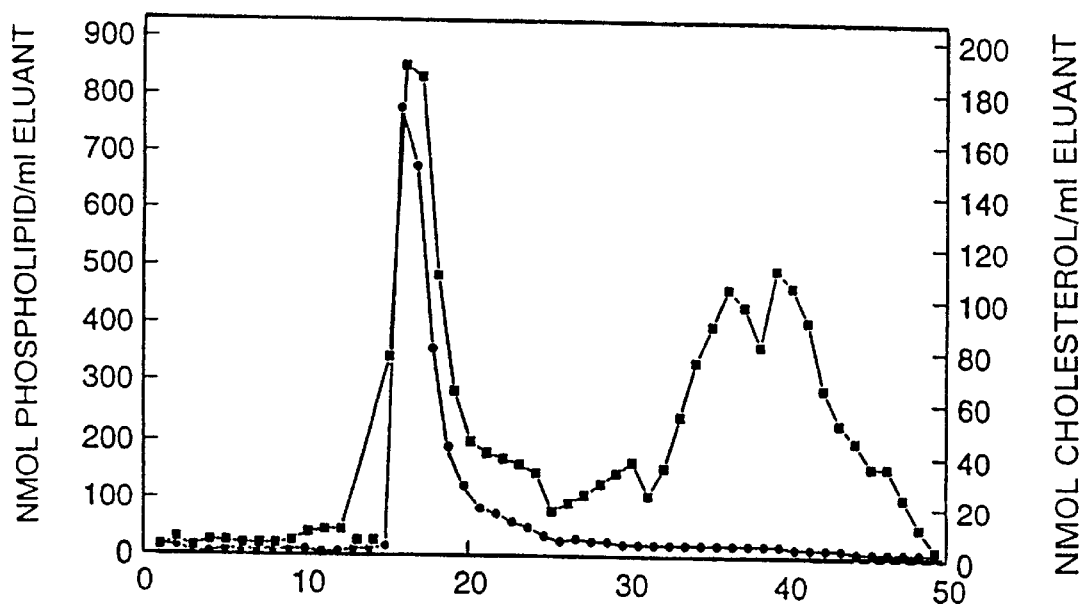

Using gel filtration as described above, mouse plasma was fractionated and the cholesterol profile determined using the chemical assay procedure of Rudel and Morris. Plasma from control and liposome-treated animals were compared and the results are shown in FIGS. 2A and 2B. FIG. 2A shows a normal cholesterol distribution with the majority of cholesterol associated with combined LDL and HDL peaks (fractions 22–50). The elution volumes of VLDL, LDL and HDL were determined as described above. A minor quantity of sterol was detected in the void volume, corresponding to the larger chylomicron and VLDL lipoprotein particles, but quantitatively these fractions represent <5% of the total cholesterol content of the plasma. The elution profile of plasma from liposome-treated animals (4 h time point) is shown in FIG. 2B. The [$^{14}$C]CHE liposome marker was almost exclusively detected in the void volume, indicating that the LUV$_{100}$ were well separated from the fractions containing LDL and HDL (liposomes smaller than 100-nm diameter are included in the gel and cannot be separated from LDL). The absence of radioactivity in the remaining fractions indicated that little, if any, assimilation of vesicles into the lipoprotein pool occurred. However, it is possible that small quantities of vesicles had undergone structural transitions to lipoprotein-like particles, but were removed rapidly from the circulation and therefore, not detected.

The cholesterol content of column fractions shown in FIG. 2B clearly shows that the excess sterol in the plasma of treated mice is associated with LUV. The slight frame shift of peaks between FIG. 2A and FIG. 2B is the result of differences in elution rate and not due to changes in lipoprotein size. Using TLC analysis it was determined that >90% of the liposomal cholesterol was free cholesterol, the remainder being cholesterol ester.

Figure 3:
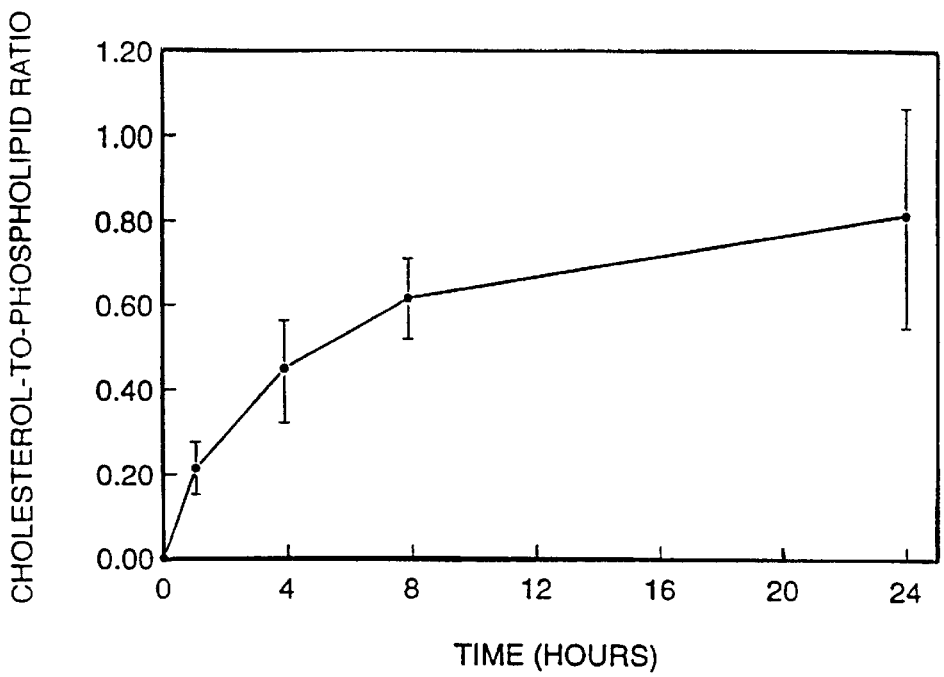
FIG. 3 illustrates liposome cholesterol accumulation over a 24-h time-course in vivo.

The excellent separation of LUV$_{100}$ from the quantitatively most abundant lipoproteins enabled straight-forward isolation and subsequent analysis of the vesicle lipids. Liposome cholesterol accumulation was shown by the increasing C/P ratio of vesicles over a 24-h time-course in vivo, as shown in FIG. 3. Consequently, after 24 h the liposomes remaining in the circulation (approx. 10–15% of the initial dose) were in equilibrium with respect to cholesterol and net sterol movement was negligible.

Plasma cholesterol concentrations were measured over a 48-h period in animals treated with a variety of liposomal preparations varying in diameter from 30–250 nm. Sonicated vesicles were prepared as described above. The remaining vesicles were produced by extrusion of MLV through filters with defined pore-sizes to give vesicle populations with the mean diameters described above. Vesicles are referred to by the filter pore size used for their synthesis.

Figure 4A:
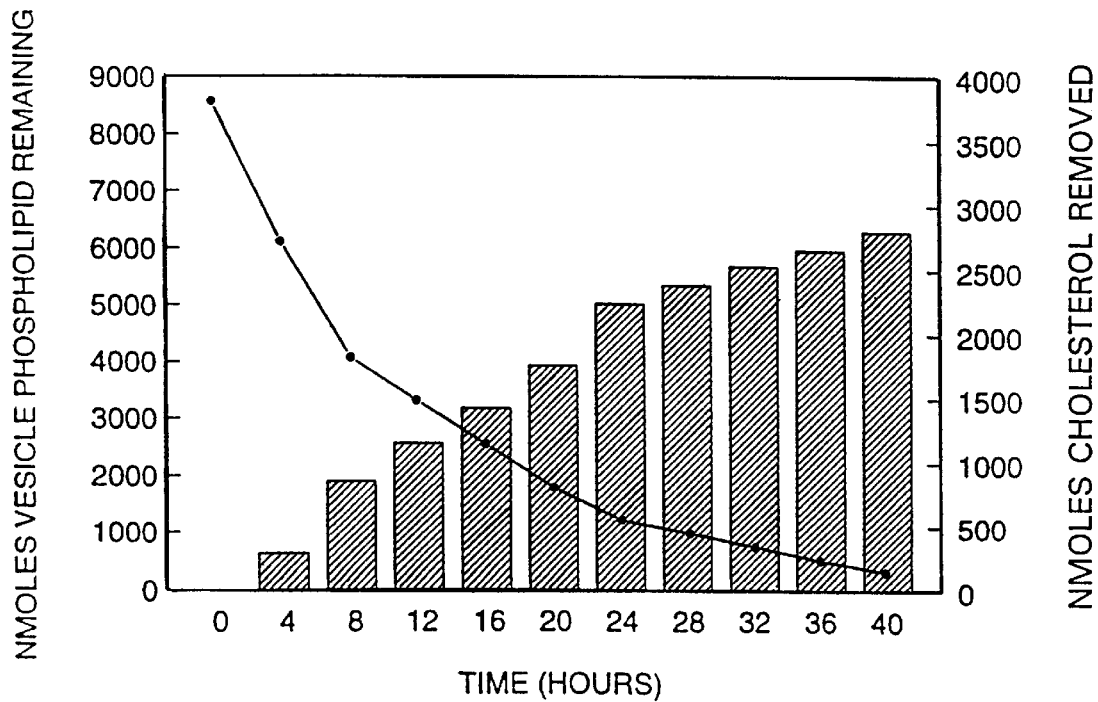
FIGS. 4A and 4B illustrate cholesterol mobilization by liposomes.
Figure 4B:
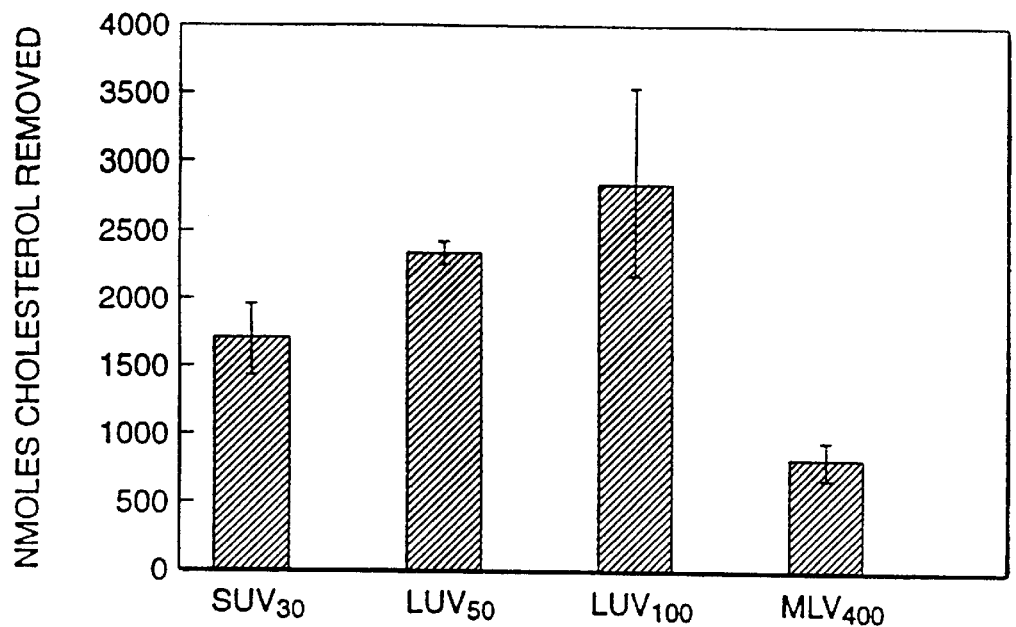

The amount of cholesterol accumulated and removed by liposomes in vivo is a function of both the rate of cholesterol uptake and the rate of liposome clearance. An estimate of the mass of cholesterol removed from the circulation (mostly by the RES) can be made by calculating the C/P ratio of vesicles in vivo from plasma concentration of vesicle phospholipid and cholesterol as the excess plasma concentration above the control at the various experimental time points. All cholesterol above control levels is associated with circulating liposomes. The plasma volume of mice used in these studies was approx. 1 ml, consequently the total amount of phospholipid cleared from the circulation between time points was known. Using the average C/P ratio measured for vesicles between each assay interval an estimate of the amount of cholesterol removed was obtained. The analysis was not continued beyond the point where less than 5% of the initial phospholipid dose remained in the circulation as below this level the measurement error was too large to determine accurate C/P ratios. FIG. 4A shows the cumulative level of cholesterol removed by $LUV_{100}$ up to the time when approx. 5% of the dose remains. After 40 h 2800 nmol of cholesterol were removed from the circulation by the RES, which represents 33 mol % of the injected phospholipid dose. This analysis was used to compare the various liposomal preparations tested. For each preparation the plasma cholesterol and phospholipid clearance profiles were determined and analyzed as described above. The results in FIG. 4B show that LUV mobilize cholesterol most efficiently.

The transfer of sterol from donor vesicles to unilamellar and multilamellar vesicles was studied. Using freeze-fracture electron microscopy and NMR analysis, it has been shown that MLV sized through 400-nm pores retain a number of internal lamellae and therefore cannot be classified as LUV. The transbilayer movement (flip-flop) of cholesterol is rapid, on the order of seconds to minutes in a liquid crystalline bilayer under conditions that promote net sterol flux. Consequently, it was expected that multilamellar systems would act as a good sink for cholesterol as sterol should rapidly disperse through the internal lamellae.

Figure 5:
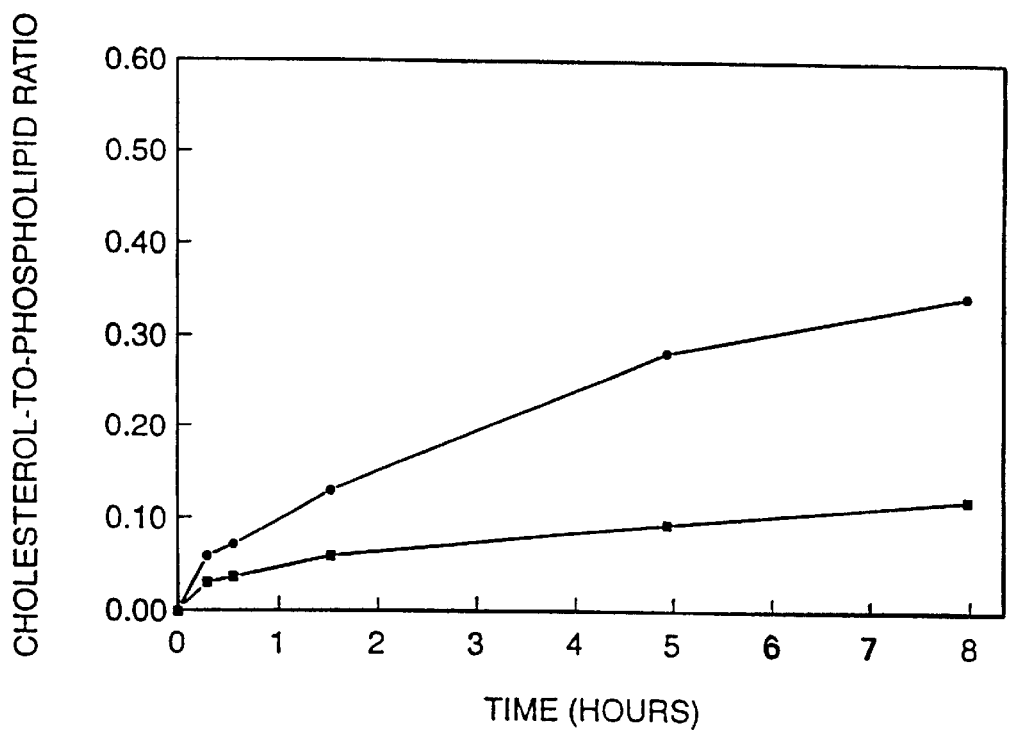
FIG. 5 illustrates a comparison of the rate of cholesterol accumulation by unilamellar and oligolamellar liposomes.

Using an in vitro model in which $LUV_{100}$ or $MLV_{400}$ were incubated with a 10-fold excess of donor liposomes containing tritiated cholesterol as described above, the net transfer of sterol from donor to acceptor was monitored. The rate of cholesterol accumulation in the unilamellar preparation was greater than that observed for the oligolamellar vesicles. It is interesting to note that in the presence of a 10-fold excess of donor vesicles the equilibrium C/P ratio of the acceptor should be approx. 0.9:1. The data in FIG. 5 show that the 100-nm acceptors only achieve a ratio of 0.35:1 after 8 h at 37° C. This is approximately half the rate of accumulation observed for the same vesicles in vivo (FIG. 3).

The cholesterol mobilizing properties of two types of $LUV_{100}$ were compared. The two types of $LUV_{100}$ were composed of EPC/EPG (95:5 mol ratio) (circles) which is liquid-crystalline at 37° C. and DSPC/DSPG (95:5). (trangles) a gel-state lipid matrix at the body temperature of the mouse. Phosphatidylglycerol (PG) was incorporated to impart a surface negative charge, necessary to prevent the gel-state vesicles from aggregating in the absence of cholesterol as described in Nayer et al., *Biochim. Biophys. Acta,* 986:200–206 (1989), incorporated herein by reference. Reliable comparison of the two systems was facilitated by adding a negative charge to the EPC vesicles. The results, presented in FIG. 6A, reveal that the gel-state vesicles produced a delayed increase in plasma cholesterol which did not peak until after 24 h, whereas EPC/EPG vesicles (circles) gave rise to a cholesterol profile similar to that observed for EPC alone.

Figure 6A:
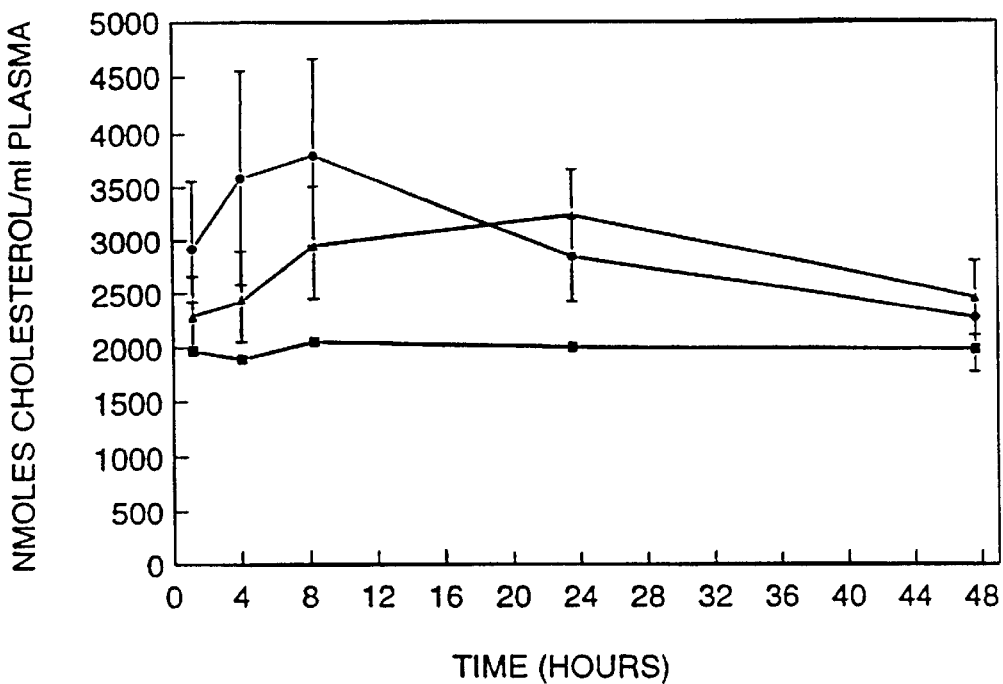
FIGS. 6A and 6B demonstrate the cholesterol mobilizing ability of liposomes having different compositions.
Figure 6B:
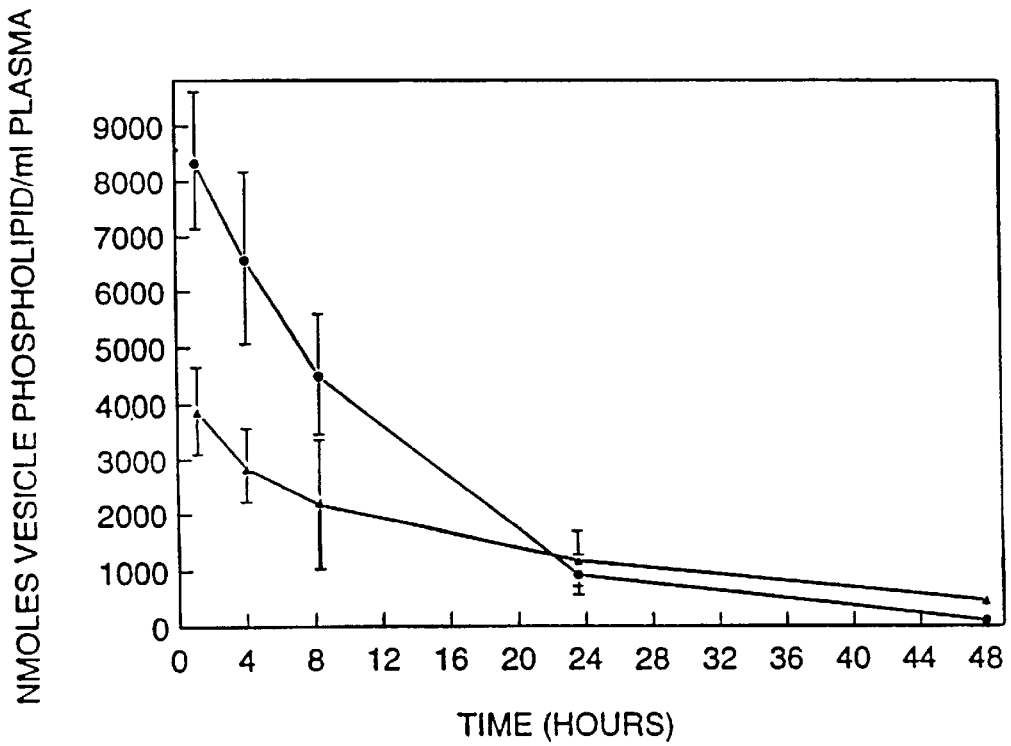

The data in FIG. 6A demonstrate that the rate of cholesterol accumulation for these two types of vesicle was the same. The different plasma cholesterol profiles occurred because approximately 70% of the DSPC/DSPG vesicles (triangles) were cleared within 4 h compared to less than 30% of the EPC/EPG $LUV_{100}$ (circles) (FIG. 6B). The bulk of cholesterol mobilization occurred in the first 24 h, consequently liquid crystalline EPC/EPG removed more than 3000 nmol to the RES, whereas DSPC/DSPG vesicles removed 1700 nmol. The source of the accumulated liposomal cholesterol and its fate was determined. Ultimately, cholesterol efflux must occur from atherosclerotic plaque to achieve regression. However, it is known that the cholesterol within cells and atherosclerotic lesions equilibrates more slowly than sterol present in plasma membranes directly exposed to acceptor particles. Movement of this cholesterol will be a secondary event initiated by the primary efflux of outermembrane cholesterol.

Figure 7A:
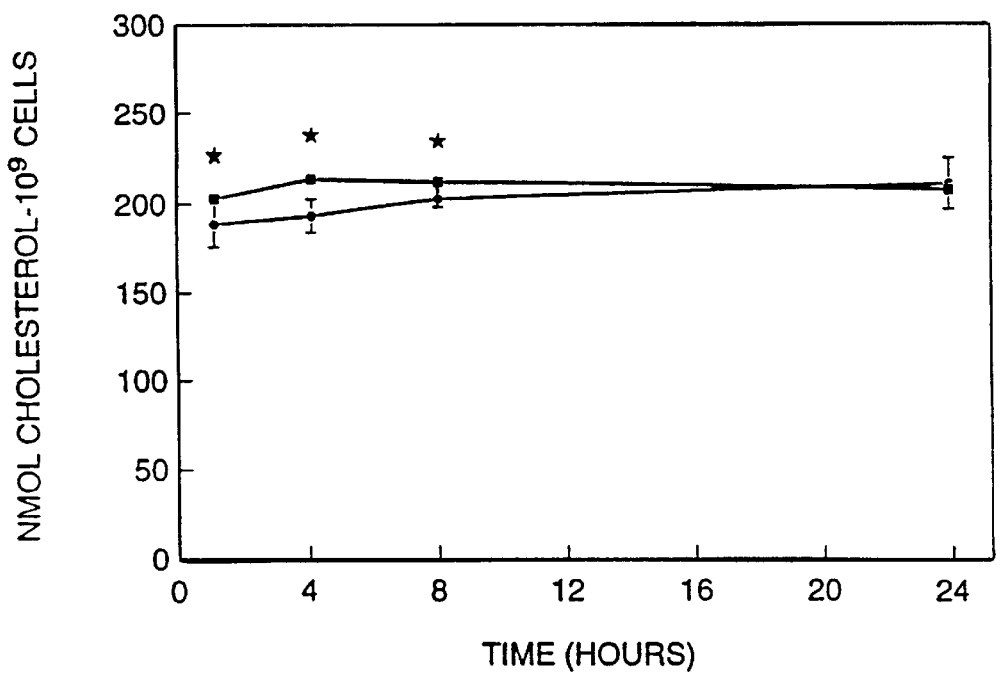
FIGS. 7A, 7B, and 7C illustrate the cholesterol content of erythrocytes in mice treated with liposomes and untreated mice.

In a 20-g mouse approximately 35% of the circulating sterol is associated with lipoproteins and about 65% with the plasma membranes of erythrocytes. However, all of the sterol associated with erythrocytes is free cholesterol, whereas a large proportion of lipoprotein sterol is esterified. Consequently, the largest pool of free cholesterol in the circulation is in the red blood cell plasma membrane. It was found that this source of cholesterol does not change significantly in the presence of liposomes, despite a two fold increase in plasma sterol concentration. This result is shown in FIG. 7A.

Figure 7B:
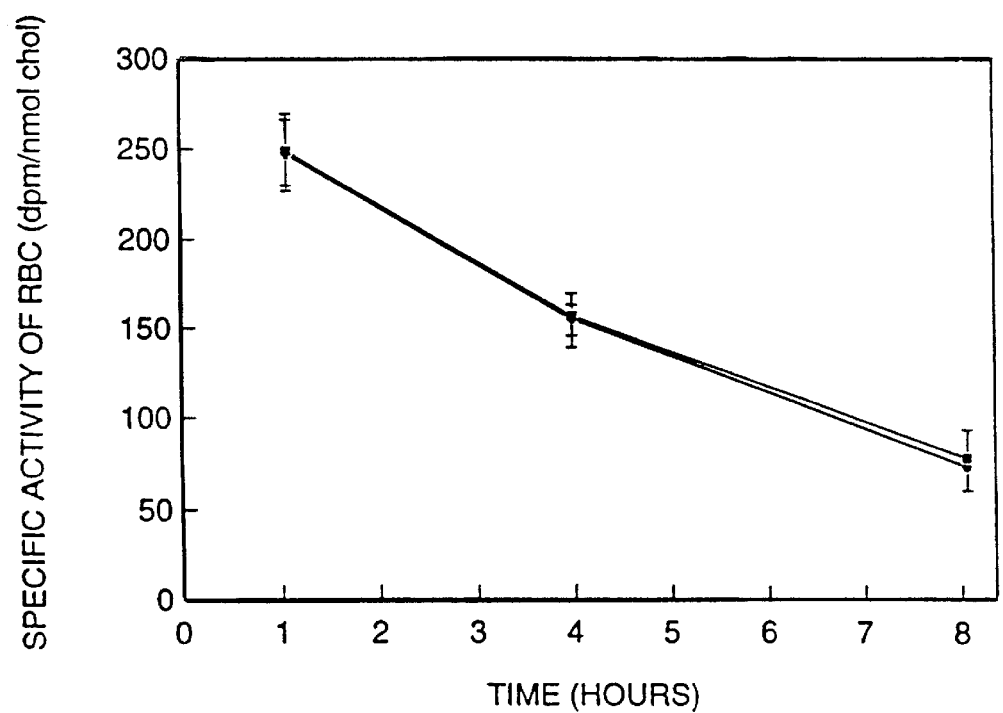

Erythrocyte membrane cholesterol can be depleted by liposomes in vitro. Consequently it was determined whether erythrocytes act as the primary sterol donor and then rapidly replenished by lipoproteins which are in turn able to extravasate and scavenge more sterol from peripheral tissues. Erythrocytes were isolated from mice and labelled with [$^3$H]cholesterol in vitro. The labelled cells were injected into a group of mice, half of which were subsequently treated with saline and half with 300 mg/kg of EPC $LUV_{100}$. The specific activity of red blood cell cholesterol was determined over an 8-h time-course and the two groups compared. As demonstrated in FIG. 7B, the decrease in cholesterol specific activity is the same for both the control and experimental group. Interpretation of these data is limited by the fact that cells labelled in vitro are also removed from the circulation over a similar time-course (determined by chromium labelling). However, it can be estimated that at least 50% efflux of cell sterol would be necessary to account for the rise in plasma cholesterol observed after 8 h. This would result in a considerable dilution of erythrocyte cholesterol if this sterol pool were continuously replenished. As this has not been observed, the data suggest that red blood cell cholesterol is not the primary source of the liposomal sterol accumulated in vivo.

Figure 7C:
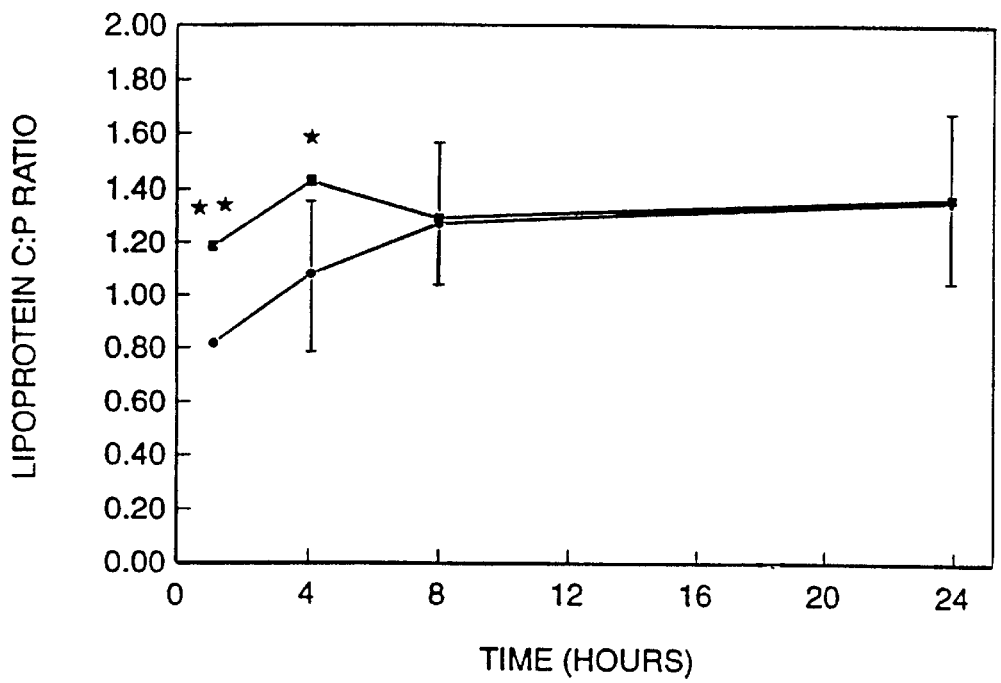

C/P ratios of lipoproteins showed a significant decrease over control values in the first 8 h (FIG. 7C). The ratio returned to normal values after 8 h mirroring the time-course of cholesterol accumulation by vesicles. This suggests that it is primarily lipoprotein cholesterol in equilibrium with circulating liposomes, and that lipoproteins mediate the transfer of cholesterol from peripheral tissues to liposomes. The results are also consistent with observations in vitro that indicate cholesterol can undergo desorption from lipoproteins more readily than from erythrocytes. Finally, the rate of cholesterol accumulation by $LUV_{100}$ in vivo (FIG. 3) is considerably faster than that observed in vitro (FIG. 5), indicating that the rate of cholesterol desorption from sources in vivo is greater than from the 100 nm vesicle donors used to obtain the data in FIG. 5.

Example 2

Regression of Atheromas in Rabbits Treated with Liposomes

This example demonstrates mobilization of cholesterol and regression of atheromas in rabbits treated with liposome compositions of the present invention. Plasma cholesterol concentration increased 2.5 times in liposome treated rabbits. Aortic lipid content decreased 25% in liposome treated animals.

Egg phosphatidylcholine (EPC) was supplied by Princeton Lipids (Princeton, N.J.). A 0.5% cholesterol supplemented diet was obtained from Teklad Premier. Blood collection tubes and butterfly needles (23 gauge) were from Becton-Dickinson (Missisauga, Ontario). Ketamine, xylazine, heparin, Innovar and Euthanyl were supplied by MTC Pharmaceuticals, Janssen Pharmaceutics and Organon Technika (Ontario). Bio-Gel A-15m was purchased from Bio-Rad. Prepacked Solid Phase silica gel columns were acquired from Burdick & Jackson. All chemical and solvents were of analytical grade from BDH Chemicals (Vancouver, B.C.).

Forty eight New Zealand White (NZW) rabbits were housed in wire cages at the Animal Unit of the Research Centre conforming to guidelines set by the Canadian council on Animal Care and the University of British Columbia. The animals were maintained in a controlled temperature environment with a 12 hour dark/light cycle. Approximately 150 g of food were given per animal per diem. Water was freely given.

Lesions induced in rabbits as a result of maintaining the animals on cholesterol enriched diets for more than two months, do not regress for lengths of up to two years even when they are returned to standard rabbit chow. St. Clair, *Prog. Cardiovasc. Dis.*, 26:109–132 (1983). Even after cessation of cholesterol enriched diets, lesions have been noted to progress and increase in complexity. Prior et al., *Arch. Path.*, 71:82–94 (1961). Moreover, in cases where intermittent feeding schedules were administered or a low cholesterol-enriched diet was given over a period of years, lesions similar to the calcified ulcerated lesions observed in humans have been produced. Constantinides et al., *Arch. Pathol.*, 70:81–92 (1961).

The correlation between hypercholesterolemia and the onset and progression of atherosclerosis in the rabbit is well established. St. Clair, supra. To ensure that an equal distribution of animals were divided into the respective treatment groups, careful pairing of the animals was done. Initially, the 48 NZW weanlings were screened for responders to the 0.5% cholesterol enriched diet (Teklad diet 0533). The animals were fed the cholesterol diet for one week and plasma cholesterol concentrations monitored until returning to normal. Animals were matched by the extent of the rise in plasma cholesterol levels as well as the rate at which the levels returned to normal. This enabled an equal distribution of animals to be placed into two groups of 24 that were fed either standard rabbit chow or 0.5% cholesterol enriched rabbit chow for 20 weeks to induce atherosclerotic plaque formation. During this time, plasma lipid levels were monitored on a monthly basis. Two animals were euthanized due to complications probably associated with handling and were excluded from the final analyses. After the diet induction period, five animals from each group were sacrificed to verify the formation of lesions and serve as the standards against which the effectiveness of liposomal treatment was assessed. Thereafter, all remaining animals were fed regular rabbit chow until the conclusion of the study.

Rabbits were fed a 0.5% cholesterol-enriched diet for 20 weeks in order to induce intermediate lesions more significant than fatty streaks associated with shorter duration cholesterol-enriched diets. Chemical and histological analyses of aortas obtained from rabbits following the diet induction period, but prior to treatment, revealed plaques formed that were rich in lipid and surrounded by fibrous tissue. These plaques consisted of almost equivalent amounts of cholesterol and cholesterol ester. The aortic phospholipid in these animals was 15±4 $\mu$mol/g wet tissue and aortic total cholesterol was 114±28 $\mu$mol/g wet tissue (61±13 $\mu$mol/g cholesterol and 53±15 $\mu$mol/g cholesterol ester). Animals maintained on a standard diet had aortic phospholipid levels of 4±0.3 $\mu$mol/g wet tissue and aortic total cholesterol levels of 10±1 $\mu$mol/g which was predominantly cholesterol. The degree of surface plaque involvement in cholesterol fed animals was 78±14%.

Based on the pairing of plasma cholesterol concentrations, 18 rabbits remaining from each diet group were separated into groups of 9 and were treated with EPC LUV$_{100}$ at a dose of 300 mg/kg or the equivalent volume of saline. Treatment was initiated 4 weeks after return to standard rabbit chow and was given over a 100 day period. The treatment consisted of ten bolus injections of phospholipid or saline administered into the marginal ear vein. One injection was given every 10 days.

The rabbits ranged from 4–6 kg in weight. Each treatment of the vesicle-receiving rabbits required the preparation of approximately 150 mls of LUV$_{100}$ at a concentration of 200 mg/ml. Typically, 6 gram aliquots of EPC were hydrated with 30 ml of filtered 150 mM NaCl, 20 mM HEPES (HBS), pH 7.4, in sterile 50 ml conical tubes, vortexed and kept overnight. As described in Example 1 above,, the resulting multilamellar vesicles (MLVs) were used to generate LUV$_{100}$ by extrusion through two stacked polycarbonate filters of 100 nm pore size using a 10 ml water-jacketed thermobarrel Extruder (Lipex Biomembranes, Vancouver, B.C.), according to the method of Hope et al., *Biochim Biophys. Acta*, 812:55–65 (1985), incorporated herein by reference. Vesicle sizes were determined by quasi-electric light scattering (QELS) analyses utilizing a Nicomp Model 370 submicron laser particle sizer (Pacific Scientific, Md.). The vesicles used for the 10 treatments had an average diameter of 114±7 nm.

A small dose of Innovar was given to promote calmness and vessel dilation in animals to ease routine bleedings necessary for plasma lipid analyses. To facilitate the final blood collections, ketamine (40 mg/kg) and xylazine (8 mg/kg) were given intramuscularly to sedate the animals. Fifty units of heparin (Hepalean) followed by a lethal dose of phenobarbital (Euthanyl) were then perfused into the marginal ear vein before laparotomy. Organs were removed, rinsed in saline and immediately frozen in liquid nitrogen. The heart and full length aorta were collected in one section and kept in iced saline. The animals were sacrificed in groups of 8–10 on alternate days. The organs were randomized prior to processing and analyses.

Each aorta was separated from the heart at the aortic valve and was carefully cleaned to remove any adherent adventitial fat. The aortas were cut along the ventral surface, opened, and photographed on a black background. The photographs were used in conjunction with the negatives to aid in the collection of digitization data as well as to facilitate the division of the aortas into three regions: the arch, thoracic, and abdominal aortic segments as described by Rosenfeld et al., *Atherosclerosis*, 8:338–347 (1988), incorporated herein by reference. Nine animals were in each of the 4 treatment groups: (1) vesicle-treated cholesterol-fed animals (VC), (2) saline-treated cholesterol-fed animals (SC), (3) vesicle-treated normal diet animals (VN) and (4) saline-treated normal diet (SN). Six aortas from each group were allocated for lipid analyses and stored at −20° C. until analysis. The remaining three samples in each group were fixed in 10% neutral buffered formalin for at least 48 hours and used for gross staining with Sudan IV and histology. Holman et al., *Lab. Invest.*, 7:42–47 (1958), incorporated herein by reference. At the time of lipid analysis, the aortas were patted dry and divided into the three segments. Wet weight and length were measured and the aortic segments were homogenized (Polytron) in HBS. Two additional washes of the Polytron probe with HBS were collected for each segment to ensure complete homogenate recovery.

Whole aortic segments were analyzed by digitization. In this analysis, photographic negatives obtained from all unstained aortas were illuminated generating an image using a Microcomputer Imaging Device (Imaging Systems). The percentage of plaque involvement was calculated by dividing the area occupied by surface plaque by the area of the entire aorta segment. Distinct differences were observed in the degree of shading of plaques and uninvolved aortic tissue. Assessments of the percentage of atherosclerotic plaque involvement were performed by two observers and the results were averaged. Interobserver variation was within ±5%.

Cholesterol and phospholipid content of the aortas and livers of the sacrificed animals were quantified following Bligh and Dyer extractions of the homogenates. Bligh and Dyer, *Can. J. Biochem. Physiol.*, 37:911–917 (1959), incorporated herein by reference. Total cholesterol, cholesterol, and cholesterol ester contents were determined according to the method of Rudel and Morris, *J. Lipid Res.*, 14:364–366 (1973), incorporated herein by reference. Cholesterol and cholesterol esters were separated by silica gel chromatography on Burdick and Jackson prepacked 200 mg Solid Phase Silica Gel columns. Cholesterol esters were eluted with 1 ml methylene chloride. Cholesterol was collected following methylene chloride/methanol (95:5) elution after transferring the columns to a new carrier. Phospholipid content was measured according to Fiske and Subbarow, *J. Biol. Chem.*, 66:375–400 (1924), incorporated herein by reference. Lipoprotein lipid profiles were quantified by enzymatic procedures after phosphotungstic acid precipitation.

Aliquots of aorta or liver homogenates were incubated overnight at 37° C. with 1 ml of 1N NaOH. Thereafter, sodium dodecylsulphate (SDS) was added to the mixture to make a 1% solution needed to solubilize any remaining particulate matter. Protein content of the samples was quantified by the bicinchoninic acid (BCA) protein assay method (Pierce Chemical Company, Rockford, Ill.) after incubation for 1 hour at 60° C. and read at $A_{562}$ against an albumin standard.

Typically, 2–3 mm segments from the arch, thoracic, and abdominal aorta of three different animals within each treatment group were divided into left and right halves and embedded in paraffin. At least 8 segments from each region were prepared as blocks, depending on the length of the aorta. Alternate sections of 5 μm were adhered to gelatin coated slides from paraffin blocks and visualized with hematoxylin and eosin (H&E) or Weigart's-van Gieson's stains. Intima/media ratios of the different regions were calculated by initially measuring an average ratio from 3 photographs generated from each section and using this value to determine a final mean±standard deviation from all the sections made from the animals of each group.

The nature of plaques from animals sacrificed after the diet induction period, but prior to any treatment was examined after sections were made from segments held into place with tissue mount (OCT) on wooden stages and quick frozen in isopentane followed by liquid nitrogen. Subsequently, alternate sections of 5 μm were adhered to polylysine coated slides and visualized with Sudan IV differentiated with Harris' hematoxylin, H&E or van Gieson's stains to highlight lipids and collagen.

Unless otherwise indicated, mean±standard deviation values are presented. The significance of the difference of the means was assessed by an analysis of variance using the two-sample t test. Only values of P<0.05 were considered significant.

Figure 8A:
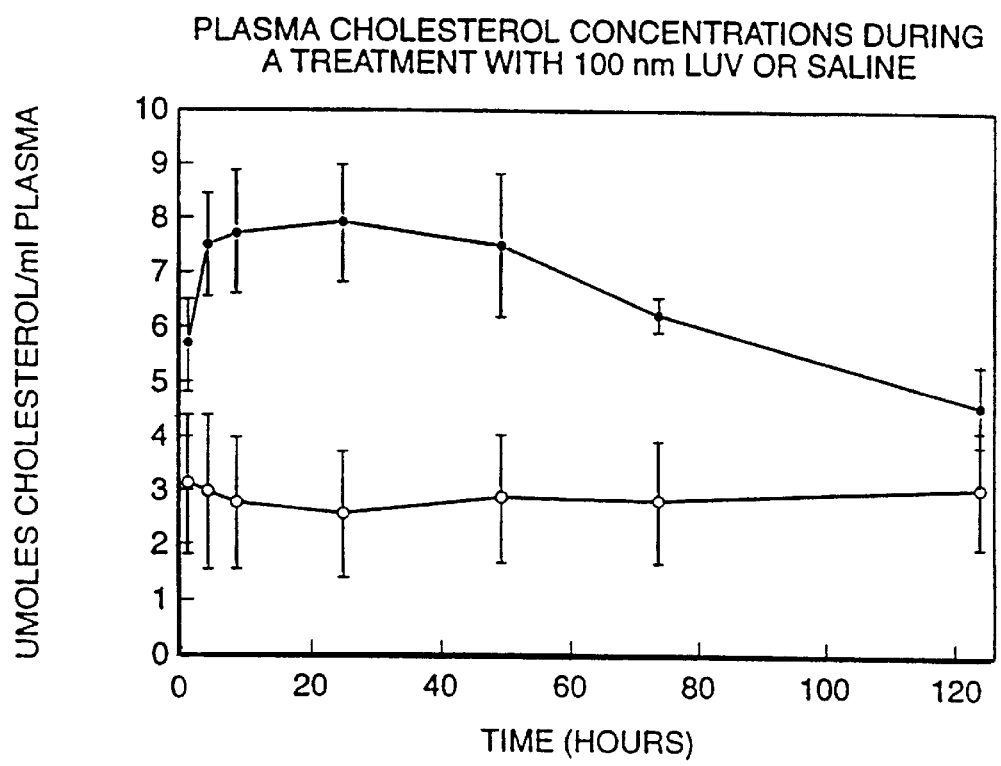
FIGS. 8A and 8B illustrate plasma cholesterol concentration changes in rabbits treated with liposomes and untreated rabbits.
Figure 8B:
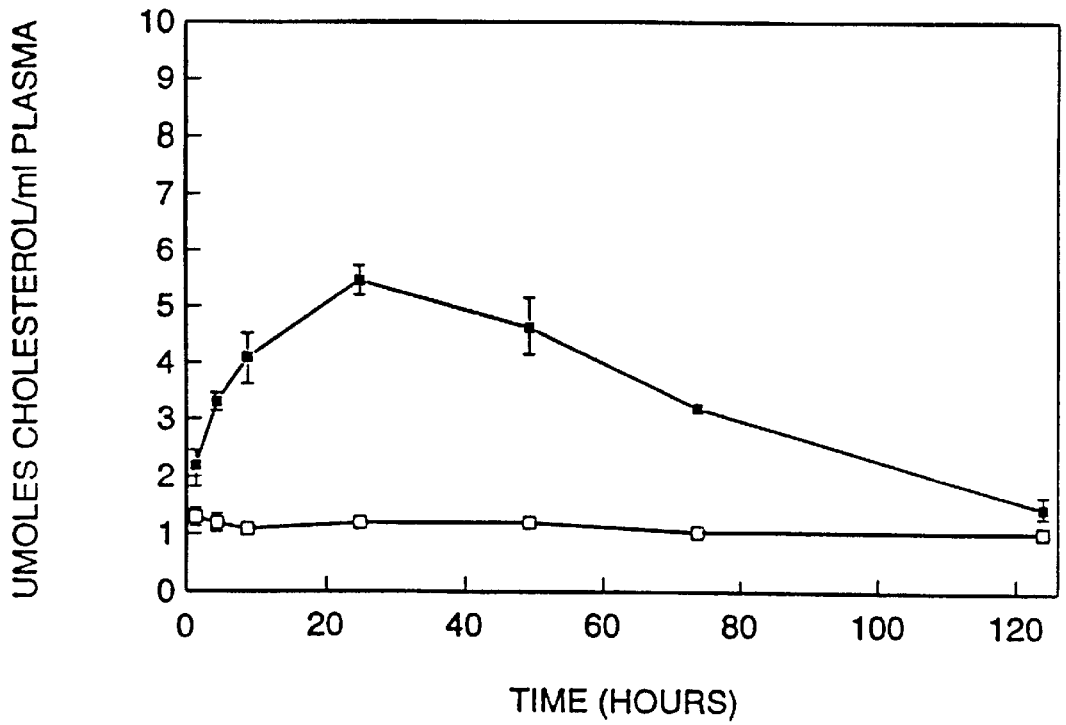
Figure 9:
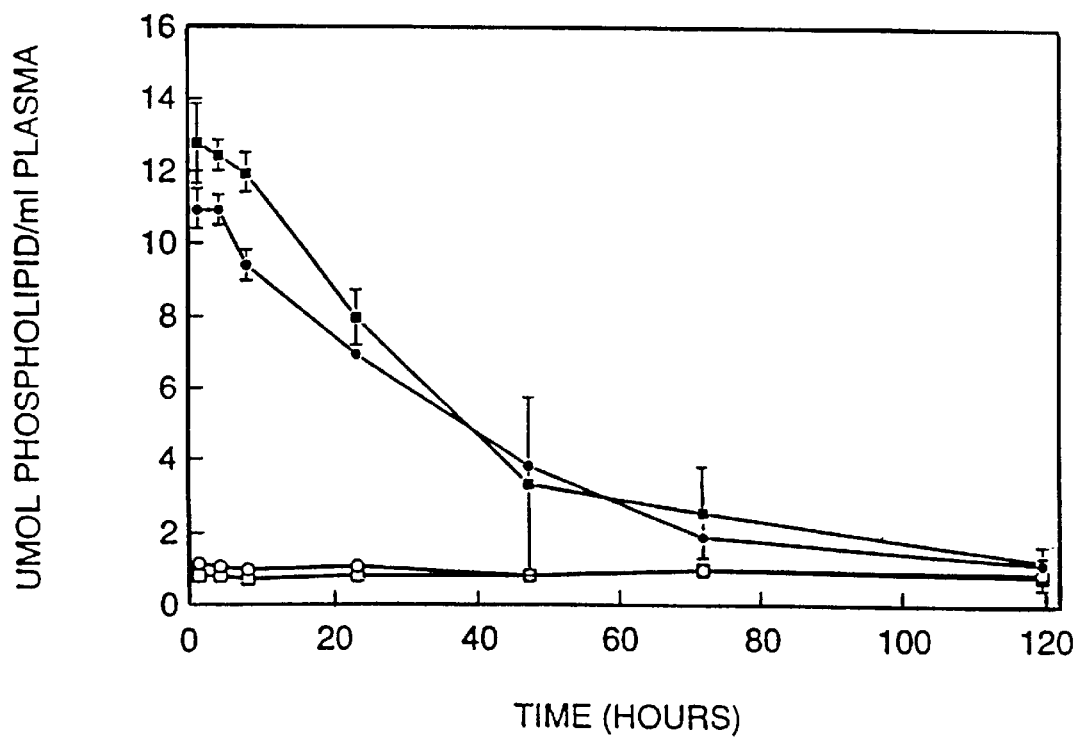
FIG. 9 illustrates plasma phospholipid concentration changes in rabbits treated with liposomes and untreated rabbits.

During the course of this study, animals maintained on the atherosclerotic diet exhibited plasma total cholesterol concentrations ranging from 5–10 times that of the control animals fed the standard diet while fed the cholesterol-enriched diet. The cholesterol concentrations remained elevated (2–5 times higher) until the conclusion of the study even though standard rabbit chow was given during the treatment period. This is illustrated in a typical time course of cholesterol mobilization resulting from the infusion of 300 mg/kg EPC $LUV_{100}$ or an equivalent volume of saline demonstrated in FIGS. 8A and 8B. A comparison of control animals injected with saline demonstrates that animals previously fed the high cholesterol diet (panel A) maintained plasma cholesterol concentrations 3 times higher than animals maintained on the standard diet throughout the study (panel B) even though the cholesterol diet was terminated 10 weeks earlier. Despite the atherosclerotic animals having excess plasma cholesterol, an injection of $LUV_{100}$ resulted in a dramatic 2.5 times increase in plasma cholesterol concentrations in both hyper- and normocholesterolemic animals when compared to saline treated counterparts. Plasma cholesterol levels peaked at 24 hours post-infusion before returning to baseline levels after 5 days. This time course correlates with the removal of vesicles from the circulation measured as total plasma phospholipid concentration illustrated in the clearance profiles shown in FIG. 9. Although atherosclerotic animals had slightly higher total phospholipid concentrations, similar clearance kinetics of the injected vesicles were seen between normal and hypercholesterolemic rabbits.

As demonstrated in Example 1 above, the amount of cholesterol accumulated and removed by liposomes with each infusion is a function of the rate of liposomal cholesterol uptake and the rate of vesicle clearance. Also, it was determined that all cholesterol above saline treated levels was associated with circulating liposomes by generating a cholesterol and phospholipid profile after separating vesicles from plasma by gel filtration. This showed that excess plasma cholesterol was associated with the vesicles and that >90% of the cholesterol was free cholesterol. Hence, an estimate of the mass of cholesterol removed from the circulation (mostly by the RES) was made by calculating the C:P ratios of vesicles at intervals following each injection from plasma phospholipid concentrations (vesicle-treated concentration minus saline-treated concentrations) and cholesterol (excess plasma concentration above the control concentration) at different time points during the experiments.

Figure 10:
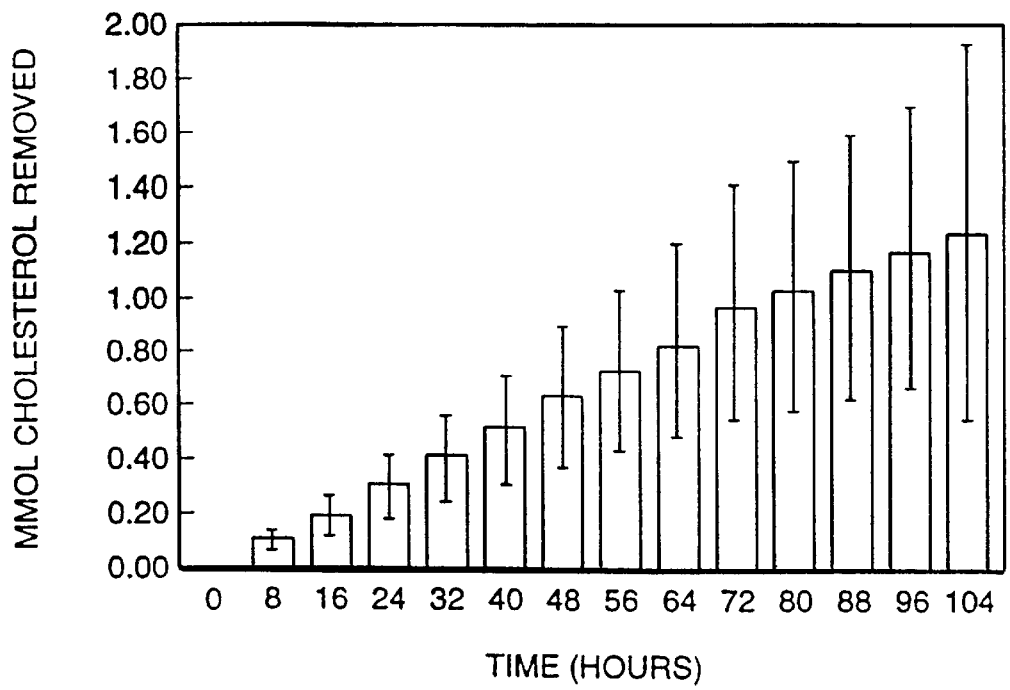
FIG. 10 demonstrates the quantity of cholesterol mobilized by liposomes during treatment of rabbits.

The plasma volume of the rabbits was approximately 150 ml. An estimate of the cholesterol removed was calculated employing the average C:P ratio measured for vesicles at each assay interval. This data is shown in FIG. 10. The data represents an average±standard deviation expressed as mmol of cholesterol removed with each treatment in hypercholesterolemic animals and was calculated from data obtained from treatments 1, 4 and 10. The analysis was not continued beyond the point where less than 10% of the initial phospholipid dose remained in the circulation. Below this level, the measurement error was too large to determine accurate C:P ratios. After 104 hours it was estimated that approximately 1 mmol of cholesterol was removed from the circulation by the RES, which represents approximately 50 mole % of the injected phospholipid dose. Furthermore, based on plasma cholesterol concentrations measured in animals 24 h post-injection, each of the 10 infusions of liposomes caused dramatic cholesterol mobilization.

The ability of the animals to tolerate and remove repeated injections of phospholipid and the consequences of administering excess phospholipid on plasma lipid levels were examined. Chronic short term (one week) administration of Intralipid, an emulsion of triglycerides and phospholipids, causes increased LDL levels. Although the phospholipid content of Intralipid is comparable to the dose of 300 mg/kg $LUV_{100}$ per injection of the present treatment regimen, Intralipid is generally given intravenously on a daily basis as a nutritional supplement.

Figure 11A:
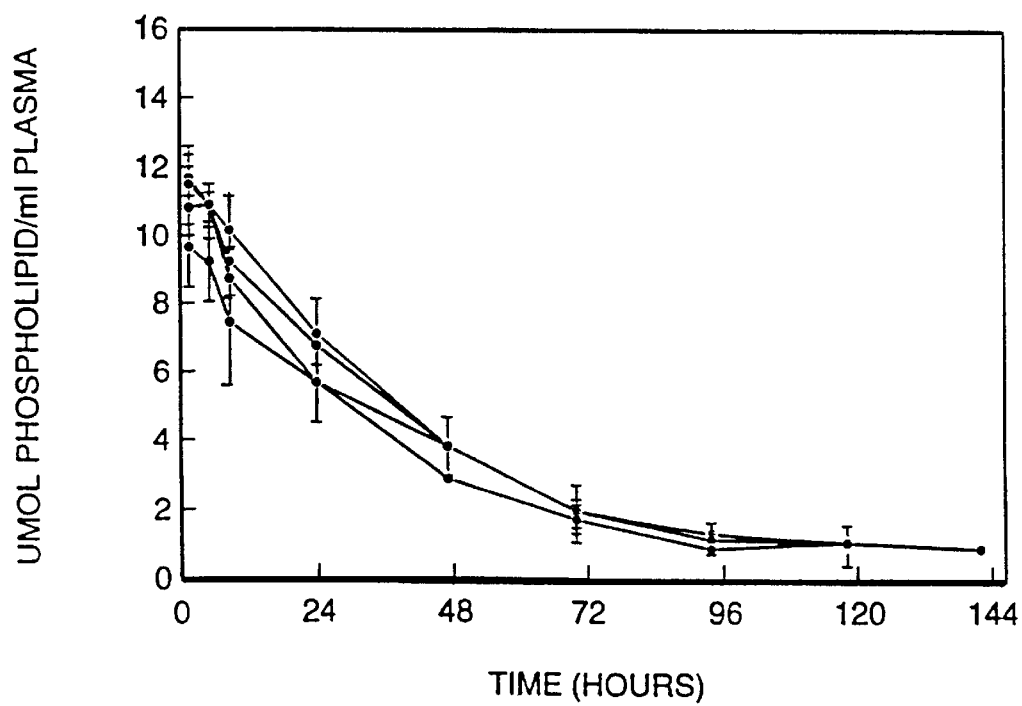
FIGS. 11A and 11B illustrate clearance profiles of liposomes injected into rabbits.
Figure 11B:
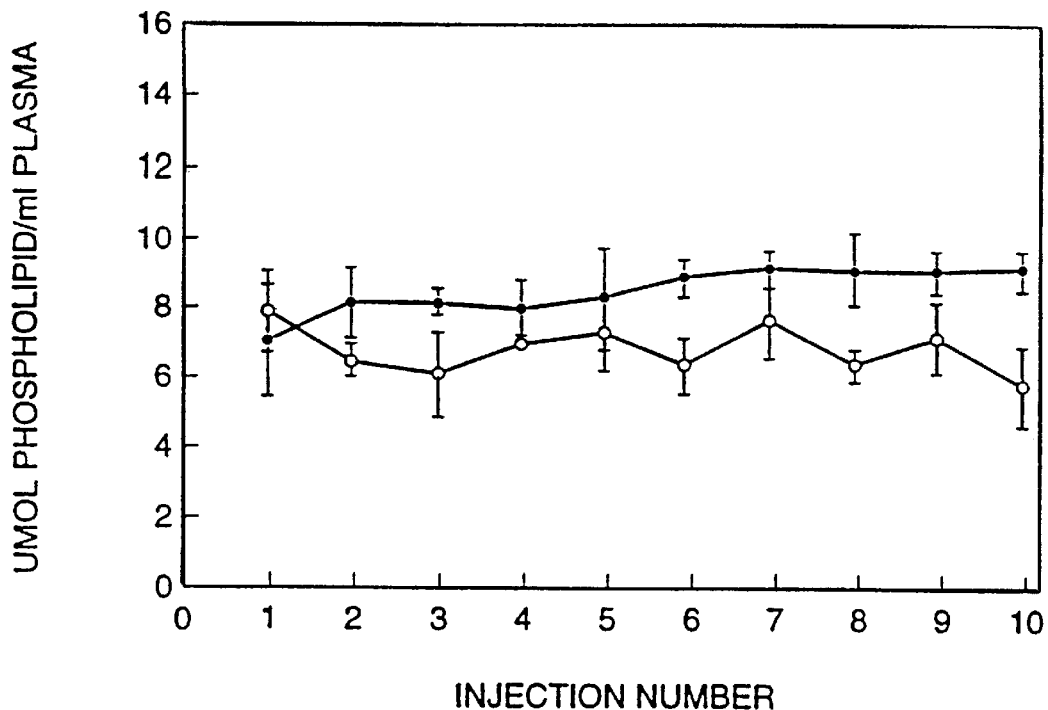

Each injection of 300 mg/kg EPC $LUV_{100}$ apparently induces a transient 100-fold increase in plasma phospholipid concentrations and at the end of liposomal therapy (10 injections) each animal received an average total dose of 12–20 mmol (10–15 g) of phospholipid. The clearance profiles of several injections of EPC $LUV_{100}$ in cholesterol fed rabbits is shown in FIG. 11A. As illustrated, significant differences in the rates of vesicle clearance between injections were not detected. FIG. 11B shows that similar concentrations of vesicle phospholipid remain in the circulation 24 h post-injection in both normo- and hypercholesterolemic animals following serial injections. If the ability of the fixed macrophages of the RES were compromised, increasing phospholipid levels would likely be detected during the later treatments. Furthermore, 5 days post-injection, the injected dose of liposome phospholipid was completely removed from the circulation and plasma phospholipid and cholesterol concentrations returned to baseline levels.

At the conclusion of the study, saline-treated cholesterol-fed animals maintained elevated plasma cholesterol levels whereas vesicle-treated animals had levels comparable to animals maintained on the standard diet. The reduction in plasma cholesterol concentrations of vesicle-treated atherosclerotic animals resulted from a reduction in both plasma LDL and HDL cholesterol concentrations although the relative proportions of HDL/LDL cholesterol were not affected. No changes in the plasma lipid profiles (cholesterol, phospholipid or triglycerides) were detected in animals maintained on standard rabbit chow throughout the study. Plasma phospholipid levels in vesicle-treated animals were similar to their saline-treated counterparts despite the injection of approximately 15 grams of phosphatidylcholine per animal during liposomal therapy. These results, unlike those observed with Intralipid infusions, suggest that repeated administration of $LUV_{100}$ given at 10 day intervals does not compromise RES function or normal plasma lipid homeostasis.

Figure 12:
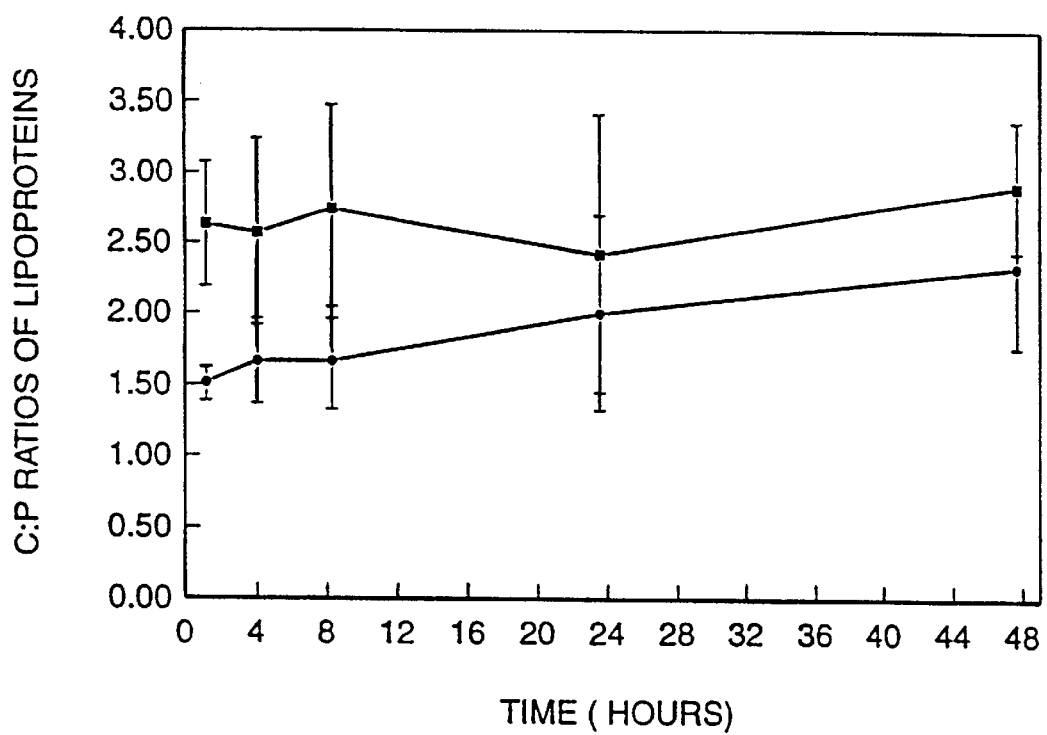
FIG. 12 demonstrates the cholesterol:phospholipid ratio of lipoproteins following liposome injection.

Erythrocyte cholesterol remained constant throughout the infusions. However, a decrease in the C:P ratios of lipoproteins was detected over the first 24 hours. This C:P reduction gradually returned to normal levels after 48 hours (see FIG. 12). This time course mirrors cholesterol accumulation by the vesicles. These results suggest that the lipoprotein pool of cholesterol rapidly equilibrates with the vesicles and supports the hypothesis that liposomes generate cholesterol-poor lipoprotein particles that can access peripheral tissues and promote cellular cholesterol efflux.

The extent of lesion progression or regression was assessed by three complementary methods: (1) chemical lipid and protein assays to determine lesion bulk, (2) digitization of gross surface morphology to quantitate the degree of plaque involvement, and (3) histochemistry to examine the nature and depth of the lesions.

Despite elevated plasma cholesterol concentrations persisting in animals returned to standard rabbit chow, saline-treated animals were found to have arterial wall cholesterol content expressed per gram wet weight of 94±12 $\mu$mol/g total cholesterol, 58±6 $\mu$mol/g free cholesterol and 37±9 $\mu$mol/g cholesterol esters with an average surface plaque involvement of 77±17%. Although there appears to be slight reduction in the cholesterol ester content, the values of the lipid content of saline-treated animals were not significantly different from values found in atherosclerotic animals prior to treatment indicating that there was no progression or regression of lesions after 4 months. On the other hand liposome-treated animals were found to have significantly less cholesterol content of the entire aorta with levels of 85±8 $\mu$mol/g total cholesterol, 48±5 $\mu$mol/g free cholesterol and 37±6 $\mu$mol/g cholesterol esters. Because there were no significant differences between the lipid content of animals before or after saline treatment, the reductions in plaque cholesterol content between liposome- and saline-treated animals indicates regression, not simply decreased progression, of plaques.

Figure 13A:
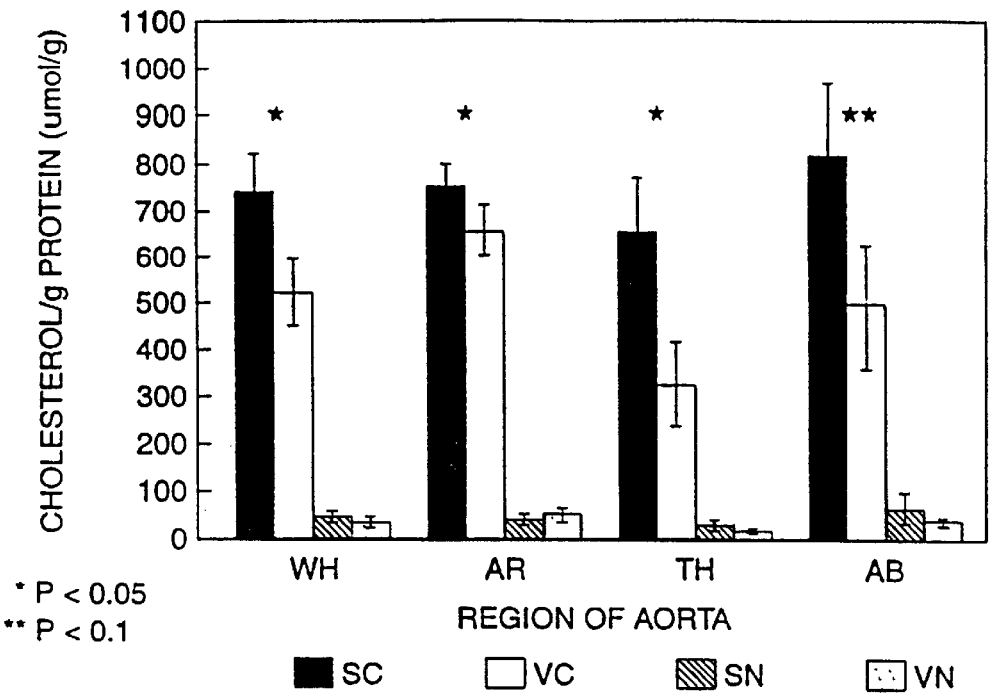
FIGS. 13A, 13B, and 13C illustrate aortic cholesterol content in liposome and saline treated rabbits.
Figure 13B:
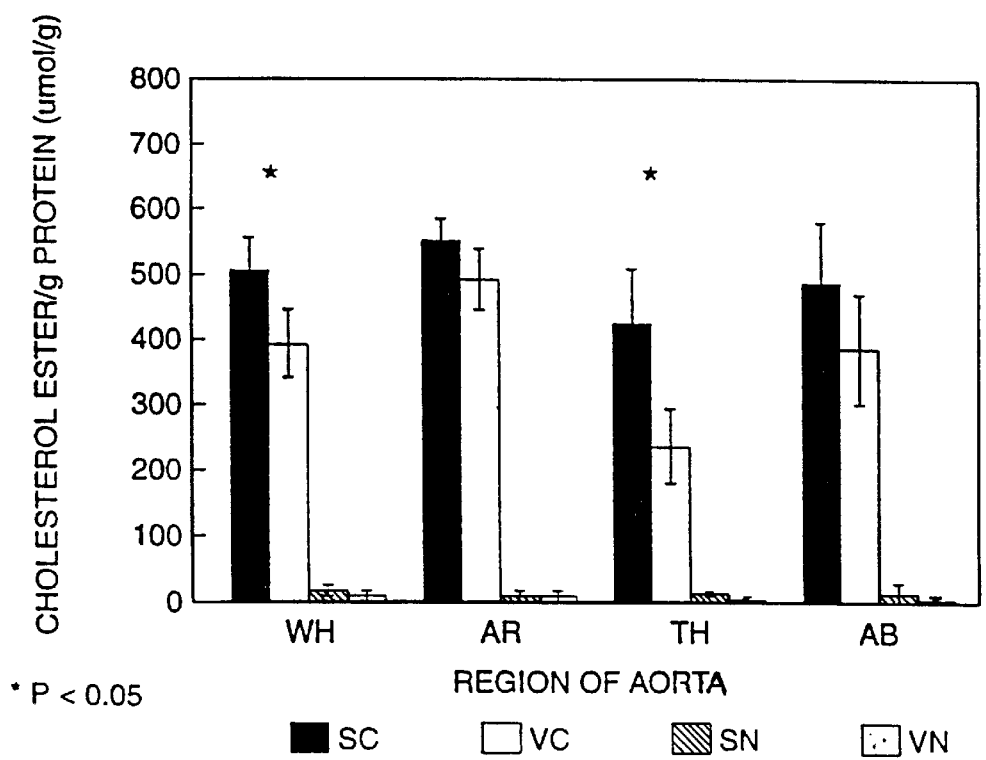

Aortic lipid content was expressed per gram of protein weight as wet weights are likely to be more variable. No significant differences were found between the protein levels in both saline- and vesicle-treated animals. The protein content of the aortas to be 0.41 g protein/g wet weight and 0.43 g protein/g wet weight, respectively. Expressing the data per g protein, liposomal therapy resulted in a 25% reduction in total cholesterol content of the entire aorta of vesicle-treated animals compared to saline-treated controls. By segment, there was a 48% reduction seen in thoracic aorta cholesterol levels and small reductions in the arch and abdominal aortas (see FIG. 13A). Significant reductions in the cholesterol ester levels in vesicle-treated animals were also noted and again the thoracic aorta demonstrated the greatest decrease (see FIG. 13B). In addition to decreased cholesterol content, aortic phospholipid levels in vesicle-treated atherosclerotic animals decreased, although not to the level of statistical significance.

Figure 13C:
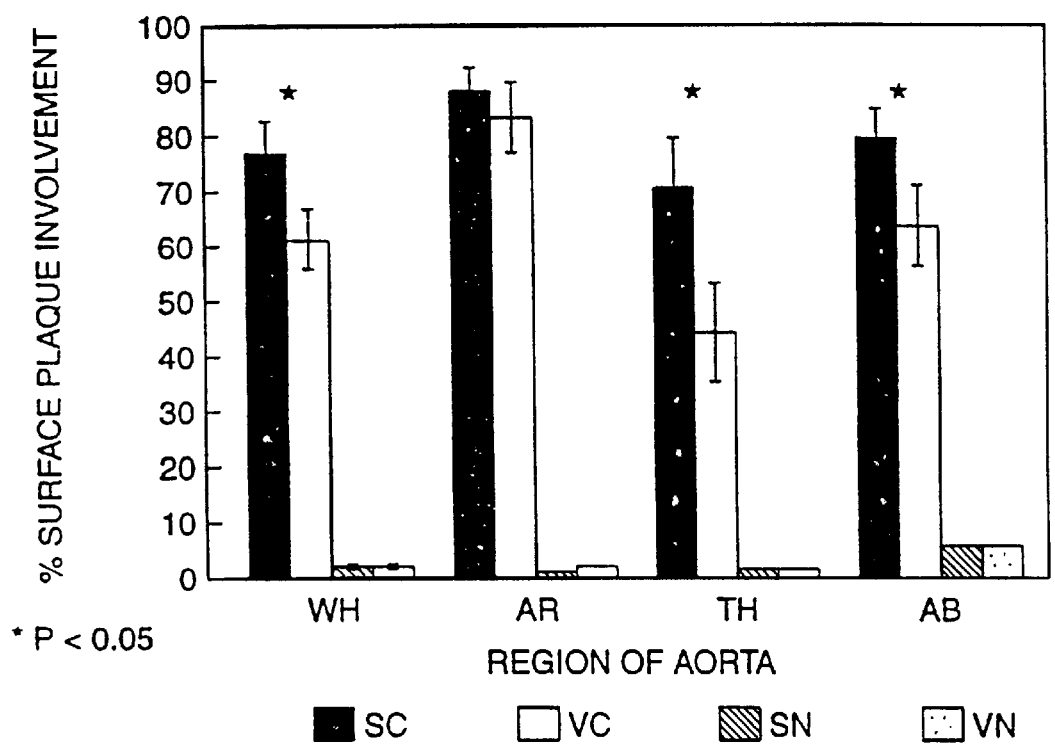

In order to maximize the number of animals within each group, all negatives generated from photographed unstained aortas were digitized. Gross Sudan IV staining of 3 aortas from each treatment group confirmed the same degree of surface plaque involvement as unstained aortas. The area of plaque involvement was determined by digitization. The data is shown in FIG. 13C. Liposome-treated, cholesterol fed rabbits demonstrated 61±13% involvement of the entire aorta compared to 77±17% involvement of saline-treated animals, representing an overall 16% reduction of surface plaque. In agreement with the reductions in cholesterol content detected by lipid analyses, the thoracic aorta exhibited the most benefit from liposome infusion with digitization analysis and displayed a 26% reduction in plaque involvement, whereas the abdominal aorta revealed a 16% reduction. There was a slight reduction in the degree of surface plaque involvement of the arch that failed to reach statistical significance. No significant differences between treated and untreated control animals maintained on the standard diet were seen and both groups showed essentially no plaque involvement.

Histochemical analysis revealed extensive raised plaques (intimal thickening) in the cholesterol fed animals as expected from gross surface morphology inspection. Whereas digitization quantitated the extent of plaque involvement, histochemical analyses allows the depth and nature of the lesions to be assessed. Generally, the plaques exhibited extensive intimal thickening due to stratified lipid deposits that were surrounded by a collagenous network. The arch region was noted to display more advanced lesions of apparent crystalline cholesterol deposits and showed a few isolated necrotic foci as detected with H&E staining.

Representative sections of the thoracic aorta of vesicle-treated and saline treated animals revealed that lesions of animals treated with vesicles manifested fewer lipid deposits and showed moderately reduced plaque thickening when compared to saline treated atherosclerotic animals. This is quantified in Table 1 summarizing the data obtained from the analysis of pictures taken from multiple sections used to assess the severity of lesions present in the arch, thoracic or abdominal aorta of atherosclerotic animals. As can be seen, a decrease in the intima/medial ratios in the arch and thoracic regions of liposome treated animals were detected, whereas no changes were detected in the abdominal aorta. No apparent differences were detected between treated and untreated animals maintained on the standard diet throughout the study.

Cholesterol feeding of rabbits often leads to the accumulation of cholesterol in a number of tissues including the liver. However upon the return to regular rabbit chow, non-arterial tissue cholesterol levels often revert to normal within a month. Liver cholesterol content was measured in order to gain insight into whether (1) increased biliary excretion of cholesterol might be occurring in liposome-treated animals due to massive deposition of the injected phospholipids in the liver resulting in reduced liver cholesterol levels or (2) there was a detrimental accumulation of cholesterol mobilized by the liposomes to the liver. In atherosclerotic animals, liposome-treated rabbits demonstrated a slight reduction in liver cholesterol content having average levels of 8 $\mu$mol/g that are comparable to control animals fed the standard diet. Saline-treated animals exhibited average levels of 11 $\mu$mol/g. This difference was not statistically significant.

All publications, patents and patent applications mentioned in this sprecification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

Table 1. Measurement of Intimal/Medial ratios in the different regions of the aorta of vesicle and saline treated atherosclerotic animals.

| Portion of aorta | Intimal/Medial Ratios | | Significance (P value) |
|---|---|---|---|
| | Liposome Treated | Silane Treated | |
| Arch | 1.51 ± 0.55 | 1.76 ± 0.94 | N.S. |
| Thoracic | 1.34 ± 0.73 | 1.93 ± 1.12 | P < 0.01 |
| Abdominal | 1.84 ± 0.95 | 1.81 ± 1.25 | N.S. |

What is claimed is:

1. A dosage formulation consisting essentially of liposomes having the structure of large unilamellar vesicles obtainable by extruding phospholipid which is in a liquid-crystalline phase at 37° C. through polycarbonate filters having a pore diameter of 0.1 micron, wherein the liposomes have a diameter of between about 100 to 150 nm, the formulation containing between about 7 and 105 grams lipid.

2. The dosage formulation of claim 1 further comprising a pharmaceutically acceptable carrer.

3. The dosage formulation of claim 1, wherein the liposomes have a average diameter of about 125 nanometers.

4. The dosage formulation of claim 1, wherein at least one phospholipid is selected from the group consisting of distearoylphosphatidylcholine, dipalmitoylphosphatidylcholine, oleoyl-palmitoyl phosphatidylcholine, palmitoyl-oleoyl phosphatidylcholine, dioleoyl phosphatidylcholine, sphingomyelin, phosphatidylglycerol, and mixtures thereof.

5. The dosage formulation of claim 1, wherein the phospholipid comprises phosphatidylcholine.

6. The dosage formulation of claim 1, wherein the liposome comprises phosphatidylcholine and phosphatidylglycerol.

* * * * *

UNITED STATES PATENT AND TRADEMARK OFFICE
CERTIFICATE OF CORRECTION

PATENT NO.    : 6,139,871
DATED         : October 31, 2000
INVENTOR(S)   : Hope et al.

It is certified that error appears in the above-identified patent and that said Letters Patent is hereby corrected as shown below:

<u>Title page,</u>
Item [63], please replace "Mar. 4, 1996" with -- Mar. 4, 1994 --.

Signed and Sealed this

Tenth Day of December, 2002

JAMES E. ROGAN
*Director of the United States Patent and Trademark Office*